US006458360B1

United States Patent
Fearon et al.

(10) Patent No.: US 6,458,360 B1
(45) Date of Patent: Oct. 1, 2002

(54) SOLUBLE COMPLEMENT REGULATORY MOLECULES

(75) Inventors: Douglas T. Fearon, Baltimore, MD (US); Thomas Hebell, Goettingen (DE)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 07/949,472

(22) PCT Filed: Apr. 4, 1991

(86) PCT No.: PCT/US91/02852

§ 371 (c)(1),
(2), (4) Date: Dec. 28, 1992

§ 102(e) Date: Dec. 28, 1992

(87) PCT Pub. No.: WO91/16437

PCT Pub. Date: Oct. 31, 1991

Related U.S. Application Data

(63) Continuation-in-part of application No. 07/513,299, filed on Apr. 25, 1990, now abandoned.

(51) Int. Cl.[7] ............................................. A61K 39/395
(52) U.S. Cl. .............................. 424/195.11; 424/192.1; 424/194.1; 435/69.7; 435/69.6; 530/350; 530/387.3; 530/395; 530/402
(58) Field of Search ................................ 530/350, 395, 530/387.3, 402; 435/69.1, 172.1, 69.7, 69.6; 424/192.1, 194.1, 195.11

(56) References Cited

U.S. PATENT DOCUMENTS

| | | | |
|---|---|---|---|
| 4,285,932 A | 8/1981 | Smith | |
| 4,642,284 A | 2/1987 | Cooper et al. | |
| 4,672,044 A | 6/1987 | Schreiber | |
| 4,704,692 A | 11/1987 | Ladner et al. | |
| 4,761,371 A | 8/1988 | Bell et al. | |
| 4,808,405 A | 2/1989 | Smith et al. | |
| 4,883,784 A | 11/1989 | Kaneko | |
| 4,894,226 A | 1/1990 | Aldwin et al. | |
| 4,937,183 A | 6/1990 | Ultee et al. | |
| 4,946,778 A | 8/1990 | Ladner et al. | |
| 5,143,901 A | 9/1992 | Schwarz et al. | |
| 5,155,027 A | * 10/1992 | Sledziewski et al. | 435/69.7 |
| 5,212,071 A | 5/1993 | Fearon et al. | |
| 5,256,642 A | 10/1993 | Fearon et al. | |
| 5,314,995 A | * 5/1994 | Fell, Jr. et al. | 530/351 |
| 5,514,582 A | * 5/1996 | Capon et al. | 435/252.3 |
| 5,565,335 A | 10/1996 | Capon et al. | 435/69.7 |

FOREIGN PATENT DOCUMENTS

| | | |
|---|---|---|
| EP | 0 325 262 | 7/1989 |
| WO | WO 88/01649 | 3/1988 |
| WO | WO 88/06630 | 9/1988 |
| WO | WO 90/04176 | 4/1990 |

OTHER PUBLICATIONS

Klickstein et al., J. Exp. Med., vol. 168, pp. 1699, 1988.*
Capon et al., Nature, vol. 337, pp. 525, 1989.*
Lowell et al., J. Exp. Med., vol. 170, pp. 1931, 1989.*
Fearon, Douglas, T. "Regulation of the Amplification C3 Convertase of Human Complement By An Inhibitory Protein Isolated from Human Erythrocyte Membrane," Proc. Natl. Acad. Sci. USA, 76:5867–5871 (1979).
Suggs, et al., "Use of Synthetic Oligonucleotides as Hybridization Probes: Isolation of Cloned cDNA sequences for Human $\beta_2$–Microglobulin," Proc. Natl. Acad. Sci. USA, 78:6613–6617 (1981).
Hewick, et al., "A Gas–Liquid Sold Phase Peptide and Protein Sequenator," J. Biol. Chem., 256:7990–7997 (1981).
Young, et al., "Yeast RNA Polymerase II Genes: Isolation with Antibody Probes," Science, 222:778–782 ((1983).
Wilson, et al., "CR1 and the Cell Membrane Proteins that Bind C3 and C4. A Basic and Clinical Review," Immunol Res., 1987, 6:192–209 (Abst. only).
Krych, et al., FASEB Journal, vol. 3, Feb. 15, 1989, Abstract 824.
Iida, et al., "Complement Receptor is An Inhibitor of the Complement Cascade", J. Exp. Med., 153:1138–1150 (1981).
Iida, et al., "Complement Receptor ($CR_1$) Deficiency In Erythrocytes From Patients With Systemic Lupus Erythematosus", J. Expt. Med., 155:1427–1438 (1982).
Dahlback, et al., "Visualization of Human C4b–Binding Protein and Its Complexes with Vitamin K–Dependent Protein S and Complement Protein C4b," Proc. Natl. Acad. Sci. USA, 80:3461–3465 (1983).
Dykman, et al., "Polymorphism of Human Erythrocyte C3b/C4b Receptor", Proc. Natl. Acad. Sci. USA, 80:1698–1702 (1983).
Medof, et al., "Role of the Complement Receptor CR1 In the Processing of Substrate–Bound C3", Ann. NY Acad. Sci., 421:299–306 (1983).
Stenlund, et al., "Secretion of the Hepatitis B Virus Surface Antigen From Mouse Cells Using An Extra–Chromosomal Eucaryotic Vector", EMBO J., 2:669–673 (1983).
Atkinson, et al., "Biosynthesis of the Human C3b/C4b Receptor During Differentiation of the HL–60 Cell Line," J. Clin. Invest., 74:1649–1657 (1984).

(List continued on next page.)

Primary Examiner—Lorraine Spector
(74) Attorney, Agent, or Firm—Leon R. Yankwich

(57) ABSTRACT

This invention is directed to a soluble recombinant fused protein which is stable in the mammalian circulatory system comprising a polypeptide which contains a recognition site for a target molecule, such as a complement receptor site, and is joined to the N-terminal end of an immunoglobulin chain. The invention is also directed to a construct comprising a plurality of peptides containing short consensus repeats having a complement binding site attached to a soluble, physiologically compatible, macromolecular carrier. The invention is particularly useful for inhibiting complement activation or complement-dependent cellular activation in mammals.

29 Claims, 24 Drawing Sheets

OTHER PUBLICATIONS

Chung, et al., "Molecular Cloning and Characterization of the cDNA Coding for C4b–Binding Protein, A Regulatory Protein of the Classical Pathway of the Human Complement System," Biochem. J., 230:133–141 (1985).

Chung, et al., "Structural and Functional Studies on C4b–Binding Protein, a Regulatory Component of the Human Complement System," Bioscience Reports, 5:855–865 (1985).

Sim, Robert B., "Large–Scale Isolation of Complement Receptor Type 1 (CR1) From Human Erythrocytes", Biochem. J., 232:883–889 (1985).

McCluskey, et al., "Cell Surface Expression of an In Vitro Recombinant Class II/Class I Major Histocompatibility Complex Gene Product", Cell, 40:247–257 (1985).

Wong, et al., "p65: A C3b–Binding Protein on Murine Cells that Shares Antigenic Determinants with the Human C3b Receptor (CR1) and is Distinct from Murine C3b Receptor," J. Immunol., 134:4048–4056 (1985).

Wong, et al., "Rapid Purification of the Human C3b/C4b Receptor (CR1) by Monoclonal Antibody Affinity Chromatography," Journal of Immunological Methods, 82:303–313 (1985).

Yoon, et al., Characterization of a Soluble Form of the C3b/C4b Receptor (CR1) in Human Plasma J. Immunol., 134:3332–3338 (1985).

Seya, et al., "Purification and Functional Analysis of the Polymorphic Variants of the C3b/C4b Receptor (CR1) and Comparison with H, C4b–Binding Protein (C4bp), and Decay Accelerating Factor (DAF)," J. Immunol., 135:2661–2667 (1985).

Wong, et al., "Identification of a Partial cDNA Clone for the Human Receptor For Complement Fragments C3b/C4b," Proc. Natl. Acad. Sci. USA, 82:7711–7715 (1985).

Wong, et al., "Analysis of Multiple Restriction Fragment Length Polymorphisms of the Gene For the Human Complement Receptor Type I", J. Exp. Med., 164:1531–1546 (1986).

Hiraki, et al., "Isolation and Characterization Of Expressible cDNA Clones For Mouse THY–1: A Model System for cDNA Expression of Cell Surface Proteins", J. Immunol., 136:4291–4296 (1986).

Holers, et al., "Human Complement C3b/C4b Receptor (CR1) mRNA Polymorphism that Correlates with the CR1 Allelic Molecular Weight Polymorphism," Proc. Natl. Acad. Sci. USA, 84:2459–2463 (1987).

Weis, et al., "A Complement Receptor Locus: Genes Encoding C3b/C4b Receptor and C3d/ Epstein–Barr Virus Receptor Map to 1q32", J. Immunol., 138:312–315 (1987).

Frank, Michael M., "Complement in the Pathophysiology of Human Disease", New Engl. J. Med., 316:1525–1530 (1987).

McLean, et al., "cDNA Sequence of Human Apolipoprotein(a) Is Homologous to Plasminogen", Nature, 330:132–137 (1987).

Kristensen, et al., "cDNA Structure of Murine C4b–Binding Protein, a Regulatory Component of the Serum Complement System," Biochemistry, 26:4668–4674 (1987).

Kristensen, et al., "The Superfamily of C3b/C4b–Binding Proteins," Federation Proc., 46:2463–2469 (1987).

Glover, et al., "Synthetic Peptide Inhibitors Of Complement Serine Proteases–I. Identification Of Functionally Equivalent Protease Inhibitor Sequences in Serpins and Inhibition of C1s and D", Mol. Immunol., 25:1261–1267 (1988).

Schasteen, et al., "Synthetic Peptide Inhibitors Of Complement Serine Proteases–II. Effects On Hemolytic Activity and Production of C3a and C4a", Mol. Immunol., 25:1269–1275 (1988).

Kumar, et al., Translation of the Human C3b/C4b Receptor mRNA in a Cell–Free System and by Xenopus Oocytes, Biochem., 28:4040–4046 (1989).

Weisman, et al., "Soluble Human Complement Receptor Type 1: In Vivo Inhibitor of Complement Suppressing Post–Ischemic Myocardial Inflammation and Necrosis," Science, 249:146–151 (1990).

Cowen, R., "Protecting Tissue From Inflammatory Attack," Science News, 138:23 (1990).

Maliszewski, et al., "Soluble Receptors for IL–1 and IL–4: Biological Activity and Therapeutic Potential", TIBTECH, 8:324–329 (1990).

Pruitt, et al., "The Effect of Soluble Complement Receptor Type 1 on Hyperacute Allograft Rejection," J. Surg. Res., 50:350–355 (1991).

Hebell, et al., "Suppression of the Immune Response by a Soluble Complement Receptor of B Lymphocytes," Science, 254:102–105 (1991).

Kalli, et al., "Mapping of the C3b–Binding Site of CR1 and Construction of a $(CR1)_2$–$F(ab')_2$ Chimeric Complement Inhibitor," J. Exp. Med., 174:1451–1460 (1991).

Xia, et al., "Prolongation of Guinea Pig Cardiac Xenograft Survival in Rats by Soluble Human Complement Receptor Type 1," Transplantation Proceedings, 24:479–480 (1992).

Hill, et al., "Soluble Complement Receptor Type 1 Ameliorates the Local and Remote Organ Injury After Intestinal Ischemia–Referfusion in the Rat," J. Immunol., 149:1723–1728 (1992).

Lindsay, et al., "Blockade of Complement Activation Prevents Local and Pulmonary Albumin Leak After Lower Torso Ischemia–Referfusion," Ann. Surg., 216:677–683 (1992).

Chaudhary, et al., "A Recombinant Immunotoxin Consisting Of Two Antibody Variable Domains Fused To Pseudomonas Exotoxin", Nature, 399:394–397 (1989).

Fries, et al., "Factor I Co–Factor Activity Of CR1 Overcomes The Protective Effect of IgG On Covalently Bound C3b Residues", J. Immunol., 135:2673–2679 (1985).

Williams, G., "Novel Antibody Reagents: Production And Potential", Trends in Biotechnology, 6:36–42 (1988).

Hebell, et al., "CR2–IgC Chimera: A Dimeric Soluble Receptor That Binds C3dg and EBV and Inhibits The Immune Response To T Independent Antigens", The Faseb Journal, 4:A1882, Abst. 1102 (1990).

Oi, et al., "Immunoglobulin Gene Expression on Transformed Lymphoid Cells", Proc. Natl. Acad. Sci. USA, 80:825–829 (1983).

Maddon, et al., "The Isolation and Nucleotide Sequence of a cDNA Encoding the T Cell Surface Protein T4: A New Member of the Immunoglobulin Gene Family", Cell, 42:93–104, (1985).

Traunecker, et al., "A Novel Approach For Preparing anti–T Cell Receptor Constant Region Antibodies", European Journal of Immunology, 16:851–854 (1986).

Williams, et al., "Production of Antibody–tagged Enzymes by Myeloma Cells: Application to DNA Polymerase I Klenow Fragment", Gene, 43:319–324 (1986).

Smith, et al., "Blocking of HIV–1 Infectivity by a Soluble, Secreted Form of the CD4 Antigen", Science, 238:1704–1707 (1987).

Dintzis, et al., "The Immunogenicity of Soluble Haptenated Polymers Is Determined By Molecular Mass and Hapten Valence", The Journal of Immunology, 143:1239–1244 (1989).

* cited by examiner

FIG. 2A

```
         90        100       110       120       130       140
AAATCCTGTGTGTCTACAGTGGTAAATATAGGGTTGTGTCTACACGATACAAAAACATGAG
..] promoter 150       160       170       180       190       200
ATCACTGTTCTCTTTACAGTTACTGAGCACACAGGACCCTCACCATGGGATGGAGCTGTAT
                                              M  G  W  S  C  I
                                             -19.....IgG leader 210       220       230       240       250       260
CATGCTCTTCTTGGCAGCAACAGCTACAGGTAAGGGGCTCACAGTAGCAGGCTTGAGGTC
 M  L  F  L  A  A  T  A  T
peptide ................-5

270       280       290       300       310       320
TGGACATATACATGGGTGACAATGACATCCCACTTTGCCTTCTCTCCACAGGTGTCCACT
                                                   G  V  H
                                                   -4
```

FIG. 2B

```
     330        ✓Pst1
CCCAGGTCCAACTGCAGCTGGGATTTCTTGT..............................
 S  Q  V  Q  L  Q  L  G  I  S  C
 <-- IgG  CR2 ----->
 1

............APPROXIMATELY 400 NUCLEIC ACIDS OF CR2.............

✓Xhol                              ✓Pst1
............CCTCTCGAGGTGAGCCAGGTCCAACTGCAGCCAGCCTGGGGCT
             P  L  E  V  S  Q  V  Q  L  Q  Q  P  G  A
            <---CR2  Hinge 1  2  3  4  5  IgG ----->
```

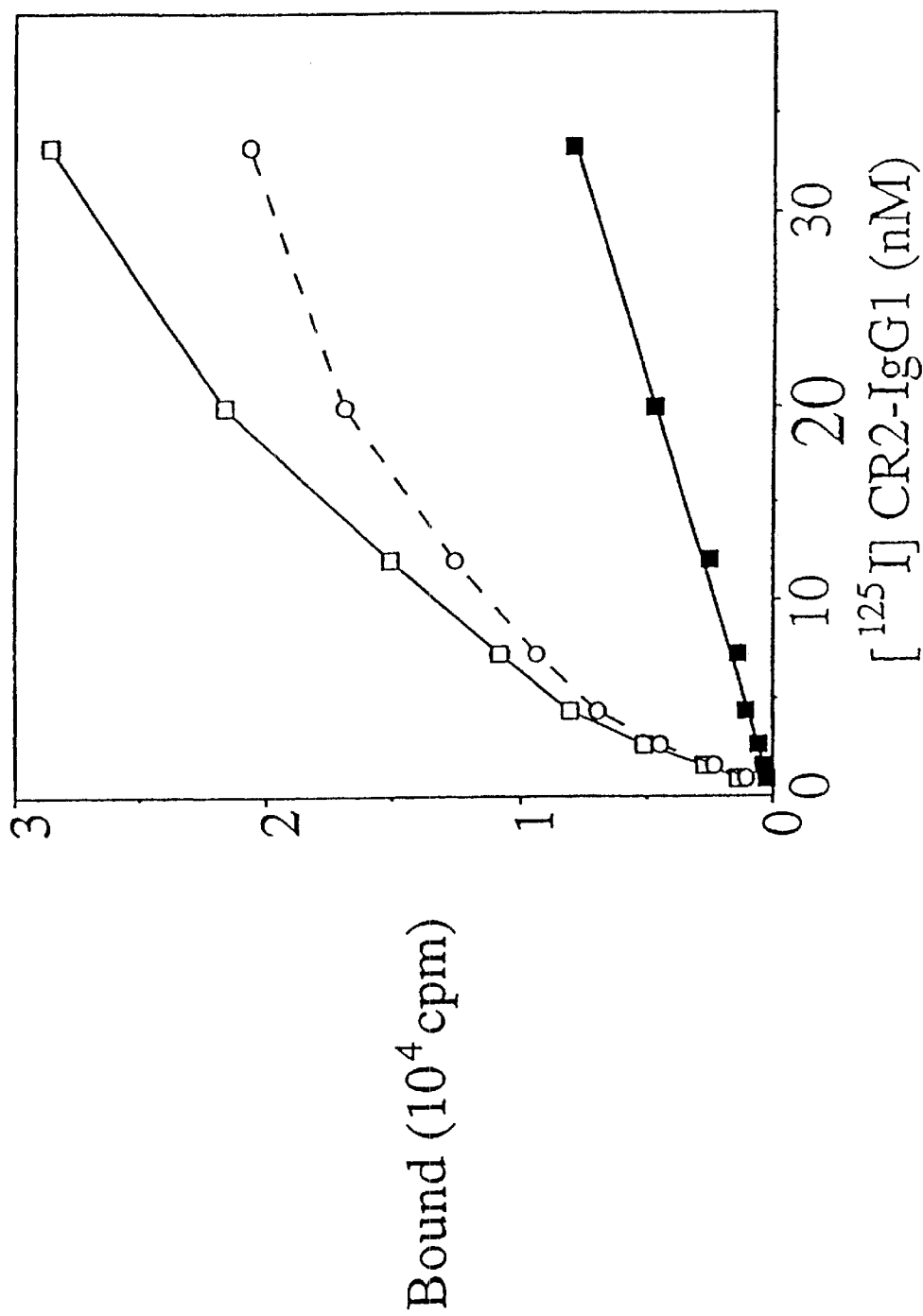

FIG. 18

```
                              PstI
............ GGT GTC CAC TCC CAG GTC CAA CTG CAG CTG GGT CAC TGT CAA GCC CCA...........
............  G   V   H   S   Q   V   Q   L   Q   L   G   H   C   Q   A   P  ..........
...IgG LEADER---IVS--  -4  -3  -2  -1   1   2   3   4   5  |----|----CR1 SCR8----
                                                           SCR 7
                                                           LAST 2
                                                           AMINO ACIDS
                                                                              PstI
............ CTA CCA AGC TGC TCC AGG GTG AGC CAG GTC CAA CTG CAG............
............  L   P   S   C   S   R   V   S   Q   V   Q   L   Q  ...........
---CR1 SCR11--------------| HINGE |  1   2   3   4   5 IgG---
```

SOLUBLE COMPLEMENT REGULATORY MOLECULES

This application is a continuation-in-part of U.S. application Ser. No. 07/513,299 which was filed on Apr. 25, 1990, now abandoned.

This invention was made with support provided by National Institutes of Health Grant Nos. AI22833 and AI28191. The U.S. Government retains certain rights in this invention.

FIELD OF THE INVENTION

This invention is directed to soluble, recombinant, fused proteins which contain a recognition site for a target molecule.

BACKGROUND OF THE INVENTION

A wide variety of different molecules are present in the mammalian circulatory system, although the precise components as well as their concentration vary from time to time. These variations in the composition of the serum are in response to a spectrum of stimuli, and by sensing the changes in serum composition and concentration, the various organs of the mammals are able to respond to the stimuli. The cells of the organism recognize changes in the circulatory system by means of cell surface receptors which bind to various molecular components of the serum. It is possible to affect the way that cells of the organism will respond to the stimuli by affecting the binding of these particular components in the circulatory system to cell surface receptors.

The Complement System

One example of a system of serum components which changes in response to environmental stimuli and whose changes are sensed through binding to cell surface receptors is the complement system. The complement system is a mechanism for the recognition of foreign materials, such as microorganisms, that proceeds through two phases: the first being the covalent attachment of two complement proteins, C3 and C4, to proteins and carbohydrates that are part of the complement-activating complex. Depending on the environmental stimuli, one of two separate pathways activates an enzyme called C3-convertase which cleaves C3, releasing the C3a peptide from the alpha polypeptide of C3 and causing a major conformational change in the C3b fragment.

The second phase is the receptor-mediated binding of these complexes by various cell types, such as lymphocytes and phagocytes. In the second phase of recognition by complement, complexes containing covalently-bound fragments of C3 and C4 are bound by cells having receptors specific for these fragments. These receptors are termed complement receptors type 1 (CR1, CD35), type 2 (CR2, CD21), and type 3 (CR3, CD11b/18). The receptors are found on the surfaces of various cell types involved in immune and inflammatory responses. By modulating the response of phagocytes and lymphocytes to microorganisms and their products, this recognition program of the complement system plays a primary role in the host resistance when activation of C3 occurs through the alternative pathway. When the classical pathway has been recruited by antibody directed to the foreign molecules, binding of complement fragments plays an amplifying role.

The SCR Motif of Complement Receptor Type 1

CR1 has been extensively studied, and a structural motif of 60–70 amino acids, termed the short consensus repeat (SCR) has been found. The SCR motif is tandemly repeated 30 times in the F-allotype of CR1 and additional repeat cycles occur in other allotypes. The consensus sequence of the SCR includes 4 cysteines, a glycine and a tryptophan that are invariant among all SCR. Sixteen other positions are conserved, with the same amino acid or a conservative replacement being found in over half of the other 30 SCRs Kliekstein, et al., (1987), *J. Exp. Med.*, (165: 1095–1112, and (1988), *J. Exp. Med.*, 168:1699–1717; Hourcade, et al. (1988) *J. Exp. Med.*, 168:1255–1270). The dimensions of each SCR are estimated to be approximately 2.53.0 nm×2 nm×2 nm.

Tandem repeats of SCRs (with the same invariant residues and similar spacing between cysteines) have been identified in 12 additional proteins of the complement system (Ahearn, et al. (1989), *Adv. Immunol.*, 46:183–219). These proteins share a capacity for interacting with C3, C4, or C5, the set of homologous complement proteins that are subunits of the alternative and classical C3–C5 convertases and the membrane attack complex, respectively. Complement proteins containing SCRs may have activating functions (C1r, C1s, Factor B and C2), negative regulatory roles (Factor H, C4-BP, DAF, MCP, and CR1), serve as cellular receptors capable of eliciting functions of phagocytes and lymphocytes (CR1 and CR2) or promote the formation of the complement channel-forming membrane attack complex (C6 and C7). thus, the SCR is one of the most characteristic structures of the complememt system. The finding of SCRs in non-complement proteins, such as the interleukin-2 receptor alpha chain, beta-2-glycoprotein 1, and factor XIII does not necessarily indicate a complement-related function, although this possibility has not been excluded.

The first 28 SCRs from the N-terminus of CR1 may be grouped into four sequential groups, each containing seven SCRs, called long homologous repeats (LHR) and designated A, B, C, and D. LHR-D is followed by the remaining two SCRs and then by a 25 amino acid transmembrane region and a 43 amino acid cytoplasmic region that serve to anchor CR1 on the cell surface. Three complement binding sites reside in CR1: one in LHR-A specific for C4b and two additional sites in LHR-B and LHR-C specific for C3b (Klickstein, et al., 1988, supra). The two N-terminal SCRs of each LHR are involved in ligand specificity. Because complement-activating substances will bind multiple C4b and C3b molecules to their surfaces, this multivalent CR1 can interact more effectively with them than would a univalent receptor.

Other Complement Receptors

Complement receptor type 2 (CR2, CD21) is a transmembrane phosphoprotein consisting of an extracellular domain which is comprised of 15 or 16 SCRs, a 24 amino acid transmembrane region, and a 34 amino acid cytoplasmic domain (Moore, et al. (1987), *Proc. Nat'l. Acad. Sci. USA*, 84:9194–9198; Weis, et al. (1988), *J. Exp. Med.*, 167:1047–1066, which are incorporated herein by reference). Electron microscopic studies of soluble recombinant CR2 have shown that, like CR1, it is an extended, highly flexible molecule with an estimated contour length of 39.6 nanometers by 3.2 nanometers, in which each SCR appears as a ringlet 2.4 nanometers in length (Moore, et al. (1989), *J. Biol. Chem.*, 34:20576–20582).

CR2 is the B-cell receptor for both the gp350/220 envelope protein of Epstein-Barr virus (EBV) and the C3dg protein fragment of complement (Ahearn, et al., 1989, supra). An anti-CR2 monoclonal antibody (OKB7) blocks binding of both C3dg and EBV, suggesting that the natural and viral ligands bind to identical or proximal sites on the receptor (Nemerow, et al. (1985), *J. Virol.*, 55:347–351). By means of recombinant DNA experiments with eukaryotic expression vectors expressing deletion or substitution mutants of CR2 in COS cells, the ligand binding sites of CR2 have ben localized in the two N-terminal SCRs of the molecule (Lowell, et al., (1989) *J. Exp. Med.*, 170:1931–1946). Binding by cell-bound CR2 of the multivalent forms of C3 ligands such as iC3B and C3dg causes activation of B-cells. (Melchers, et al. (1985), *Nature*, 317:264–267; Bohnsack, et al. (1988), *J. Immunol.*, 141:2569–2576; Carter, et al. (1988) *J. Immunol.*, 457–463; and Carter, et al. (1989), *J. Immunol.*, 143:1755–1760).

A third complement receptor, CR3, also binds iC3b. Binding of iC3b to CR3 promotes the adherence of neutrophils to complement-activating endothelial cells during inflammation (Marks, et al. (1989), *Nature*, 339:314). CR3 is also involved in phagocytosis, where particles coated with iC3b are engulfed by neutrophils or by macrophages (Wright, et al. (1982), *J. Exp. Med.*, 156:1149; (1983) *J. Exp. Med.*, 158:1338).

Soluble Complement Receptors

CR1 is a candidate for effective inhibition of complement activation. Only CR1 combines specificity for both C3b and C4b with capabilities for dissociating the C3 convertases of both pathways and for cofactor activity in the proteolytic inactivation of C3b and C4b by factor I. In addition, and probably of critical importance, these functions of CR1 are not restricted by alternative pathway activating functions, making the receptor suitable for suppressing activation by non-immunologic stimuli.

Soluble CRI (sCR1) fragments have been prepared by recombinant DNA techniques, using cDNA lacking the transmembrane and cytoplasmic domains (Fearon, et al., International Patent Application WO 89/09220, published Oct. 5, 1989), Weisman, et al., *Clin. Res.*, 38:287A, 1990). A purified sCR1 protein produced from the vector pBSCR1c in Fearon et al., 1989 (hereafter called sCR1/pBSCR1c), bound dimeric $^{125}$I-C3b and $^{125}$I-C4b with Kds (equilibrium dissociation constant) of 1 nM and 1 nM, mediated cleavage by factor I of these proteins, and in nanomolar concentrations, inhibited classical and alternative pathway activation in human serum, indicating that its ligand building sites were intact and that it had potent in vitro inhibitory function (Weisman, et al., 1990,supra)).

In vivo complement inhibitory functions of sCR1/pBSCR12c were studied in the rat model (Weisman, et al., 1990. supra)). sCR1/pBSCR1c blocked complement activation, reduced inflammation as exemplified by decreased neutrophil accumulation in the ischemically damaged myocardium, and diminished tissue injury. Recombinant sCR1/pBSCR1c attenuates tissue damage in inflammation secondary to ischemia; it recommends itself for use in treatment of more complex autoimmune diseases known to be complement-dependent, such as immune complex-induced vasculitis, glomerulonephritis, hemolytic anemia, myasthenia gravis, rheumatoid arthritis and multiple sclerosis.

Attempts to produce a soluble CR2 analogue, have ben made (Moore, et al. (1989), J. Biol. Chem., 264:20576–20582). In analogy to the soluble CR1 system, soluble CR2 was produced in a recombinant system from an expression vector containing the entire extracellular domain of the receptor, but without the transmembrane and cytoplasmic domains. This recombinant CR2 is reported to bind to C3dg in a 1:1 complex with Kd equal to 27.5 micromolar. The binding affinity for C3dg, however, is far too low for any therapeutic application.

Soluble Receptors as Antiviral Agents

There are numerous advantages in the use of soluble viral receptors to block acute viral infection. Since variants of the virus must recognize the same cell receptor use of soluble receptors will circumvent antigenic changes and polymorphism of viral envelope proteins or strain variation. Further, the viral-binding domain(s) of cellular receptors would not likely be antigenic, toxic, or immunosuppressive. (Nemerow, et al. (1990) *J. Virol.*, 64:1348–1352). Because the soluble receptor is not used as an immunogen, effectiveness would not require the use of adjuvants, and furthermore, efficacy would not be dependent on the presence of an intact immune system.

CR2 is one of the primary determinants of Epstein-Barr virus tropism because it specifically binds virions to the cell membrane. Soluble CR2 was produced in a recombinant system from an expression vector containing the entire extracellular domain of the receptor, but without the transmembrane and cytoplasmic domains. This recombinant CR2 is reported to bind to the Epstein-Barr proteins gp350/220 in a 1:1 complex with Kd=3.2 nM. (Moore, et al. (1989), *J. Biol. Chem.*, 264:20576–20582).

The attempt to block viral binding by administering a soluble form of the membrane-bound receptor protein for a virus has been explored in other viral systems, particularly in AIDS. The AIDS virus receptor protein, CD4, was prepared in soluble form by recombinant methods, using DNA encoding the extracellular domain but not the transmembrane region or the cytoplasmic region (Hussey, et al. (1988), *Nature*, 331:78–81). This recombinant protein was successful in blocking AIDS infection of cultured cells, but when injected into patients, the recombinant protein was rapidly cleared, with the half-life of the major phase of drug elimination being approximately 1 hour (Kahn, et al. (1990), *Ann, Intern. Med.*, 112:254–261).

Hybrid Immunoglobulin Proteins

In order to overcome the short-half life of soluble CD4, hybrid molecules were prepared by recombinant DNA technology in which DNA encoding the binding region of CD4 was substituted for DNA encoding the variable region of a murine immunoglobulin molecule (Capon, et al. (1989), *Nature*, 337:525–531 and WO89/029922). This is possible because CD4 is itself part of the immunoglobulin gene superfamily, and therefore it has a homologous structure to the variable region that was replaced. The CD4 hybrid based on murine immunoglobulin showed a substantial increase in the serum half-life in rabbits compared to soluble CD4.

Hybrid antibodies were also produced by Bruggemann, et al. (1987, *J. Exp. Med.*, 166:1351–1360), to study the effect of changes in various parts of the molecule on the function of antibodies where the antigen binding region is held constant. Here again, the structure of the peptide sequence inserted into the immunoglobulin molecule was similar to that of the peptide which it replaced. The study showed that regions of the immunoglobulin structure can be substituted with homologous structures without disrupting the structure of the whole molecule.

In order to obtain enough T-cell receptor protein for biochemical studies, Gascoigne, et al. (1987), *Proc. Natl. Acad. Sci. USA*, 84:2936–2940) constructed an expression vector encoding a hybrid T-cell receptor-immunoglobulin protein. The T-cell receptor is a member of the immunoglobulin gene superfamily, encoded by a genomic DNA composed of a number of similar gene segments which rearrange to form the final coding sequence for the receptor protein. The final rearranged sequence has variable, diversity and joining segments in parallel with immunoglobulin genes.

The hybrid receptor protein was constructed by replacing the variable region of an expression vector for a heavy immunoglobulin chain with the rearranged variable region of a T-cell receptor. This vector was then expressed in a cell line which only secreted the light chain. The transformed cell line secreted a chimeric protein which had both immunoglobulin and T-cell receptor determinants.

The above prior art substituted only DNA sequences encoding peptide domains which have similar homology units to immunoglobulin peptides derived from the immunoglobulin gene superfamily (Hood, et al. (1985), *Cell*, 40:225–229). The DNA sequences corresponding to a homology unit(s) of the immunoglobulin chain were removed and replaced by DNA encoding a similar homology unit from another protein of the immunoglobulin supergene family without disrupting the ability of a host cell to express the hybrid protein.

SUMMARY OF THE INVENTION

It is one object of this invention to provide a soluble protein capable of specifically binding a target molecule, said protein having a good half-life of clearance from the mammalian circulatory system.

It is another object of this invention to provide a soluble protein capable of specifically binding the target molecule, said protein having an enhanced affinity for the target molecule.

It is a further object of this invention to provide a soluble construct capable of specific multivalent binding to complement proteins.

It is still another object of this invention to provide a soluble construct with a compact structure which will be better able to diffuse into tissues from intravascular space.

It is yet another object of this invention to provide a soluble construct which will compete with the cell-bound receptors and which will persist in the mammalian circulatory system.

It is a further object of this invention to provide a method for inhibiting complement-dependent cellular activation in animals by administration of a soluble construct which is stable in the circulatory system.

It is yet another object of this invention to provide a method for inhibiting complement activation in animals by administering a soluble construct which is stable in the circulatory system.

In one of its aspects, this invention contemplates a soluble recombinant fused protein which is stable in the mammalian circulatory system comprising a polypeptide which contains a recognition site for a target molecule and is joined to the N-terminal end of an immunoglobulin chain. The use of the recombinant fused protein in therapy is also contemplated.

In a related aspect, this invention contemplates an expression vector and a method for producing an expression vector encoding the recombinant fused protein which comprises modifying an expression vector for an immunoglobulin chain by inserting a DNA sequence encoding a binding or recognition site between the DNA sequence encoding the leader peptide and the DNA sequence encoding the N-terminal end of an immunoglobulin chain. A host cell is also contemplated which contains the vector, the cell preferably expressing a complementary immunoglobulin chain, so that a complete immunoglobulin molecule or fragment is secreted which carries the binding or recognition site fused to the N-terminus of at least one immunoglobulin chain.

The recombinant fused protein of this aspect of the invention is soluble and will be relatively stable in aqueous medium, particularly he mammalian circulatory system, because of the stability and solubility of the immunoglobulin molecule. Where the recombinant fused protein is secreted as part of an antibody molecule, said molecule possesses polypeptide recognition moieties attached to the N-terminal ends of at least two of the four immunoglobulin chains present and also possesses the enhanced binding affinity for the target molecule which multivalency confers. The flexibility inherent in the immunoglobulin structure, particularly due to the hinge portion of the antibody molecule, permits movement of the polypeptide binding moieties relative to each other to facilitate adaptation of the three-dimensional arrangement of binding sites to the three-dimensional arrangement of complementary sites on the target.

While the use of a recombinant fused immunoglobulin protein containing multiple short consensus repeats having a complement binding site is a preferred embodiment of the invention, the invention also more broadly contemplates constructs comprising a plurality of peptides containing short consensus repeats having a complement binding site attached to a soluble, physiologically compatible carrier and the use of such constructs in therapy.

Such constructs provide significant benefits with respect to enhancing binding affinity by presenting multiple binding sites (multi-valency). The enhanced affinity of the constructs of this invention provides important benefits when the constructs are used in therapy. Such benefits are particularly important for therapy employing short chain repeats derived from CR2 since mature CR2 contains only a single binding site with low affinity.

BRIEF DESCRIPTION OF THE DRAWINGS

FIGS. 2A and 2B. Detail of the DNA sequence modifications introduced into the gamma-1 genomic DNA when constructing the plasmid for CR2-IgG1.

FIGS. 10A and 10B. Binding of [$^{125}$I] CR2-IgG1 to zymosan particles bearing human or murine C3 fragments. (A) Incremental concentrations of [$^{125}$I] CR2-IgG1 were incubated for 30 min. at 0° with 1.3×10⁷ zymosan particles, that had been reacted with human serum in the presence of $Ca^{2+}$ and $Mg^{2+}$ to permit activation of the alternative pathway (open square) or in the presence of EDTA to block activation (filled square). Bound and free ligand were separated by centrifugation of the particles through 10% BSA. Specific binding of [$^{125}$I] CR2-IgG1 to particle-associated C3 fragments (open circle) was calculated as the difference between the amounts bound to particles that had been reacted with serum in the presence or absence of cations, respectively. The date represents the means of duplicate determinations. (B) [$^{125}$I] CR2-IgG1 was assessed in parallel for its capacity to bind to zymosan particles that had been reacted with murine serum in the presence of divalent cations (open square) or EDTA (filled square) and specific binding (open circle) was calculated as in the experiment depicted in (A).

FIG. 18. The sequence of the CR1-F(ab')₂ construct is depicted. The Pst I sites are indicated. Nucleotides 1501 through 2262 of CR1 containing SCRs 8 through 11 were cloned into the Pst I site of the vector. IVS=IgG leader intervening sequence; nucleotides are numbered such that the CR1 leader=nucleotides 28–150 and the N-terminus of CR1=nucleotide 151.

DETAILED DESCRIPTION

Figure 1:
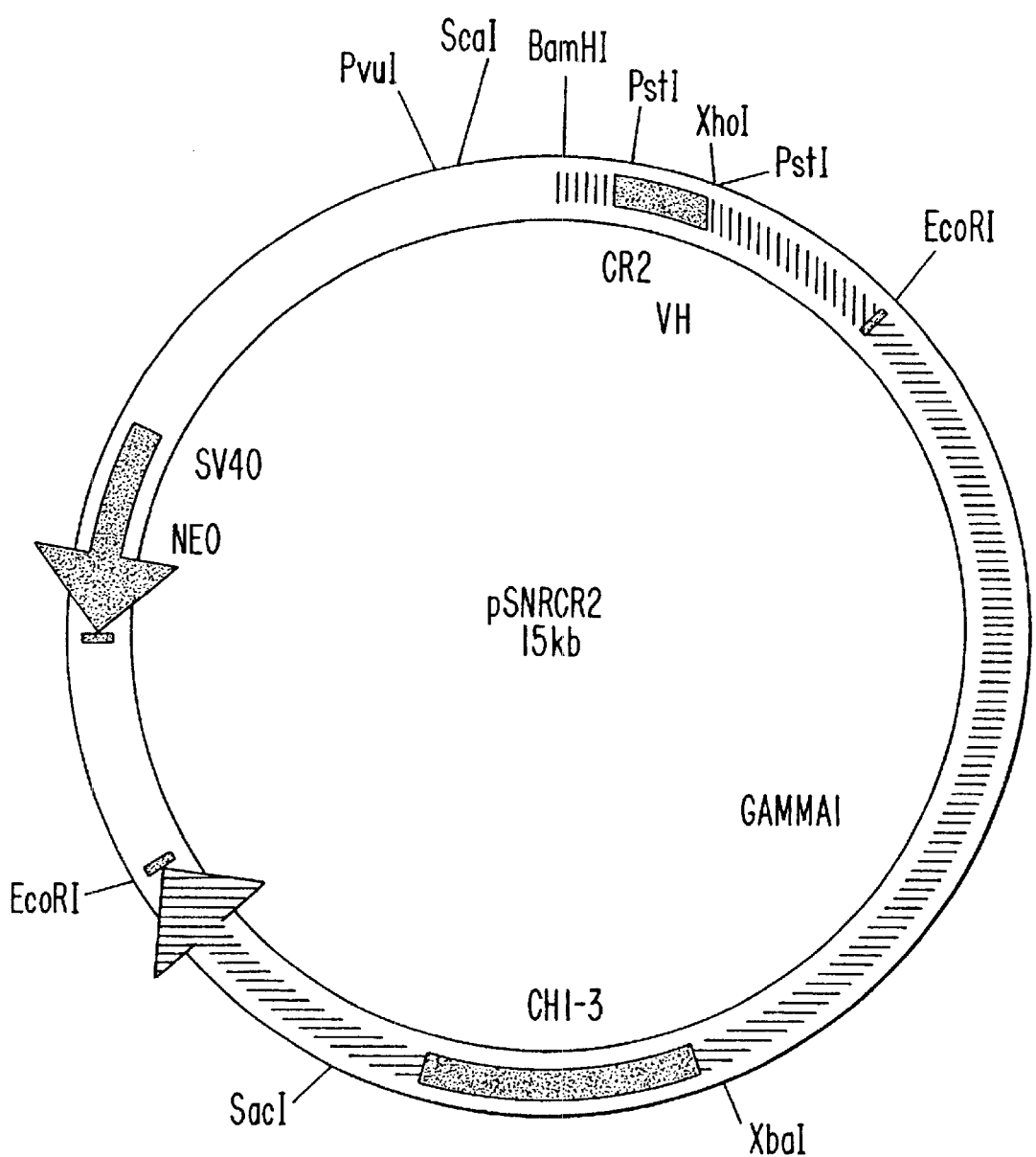
FIG. 1. Map of the plasmid constructed for expression of the CR2-IgG1 fusion protein. CR2: complement receptor type 2; VH: variable heavy chain; gamma 1: constant heavy chain, CH1–3: coding region of the constant heavy chain; NEO: gene encoding for G418 resistance; SV40: simian virus 40 promoter.

One aspect of this invention contemplates a fusion protein in which a polypeptide having a recognition site for a target moiety is attached to the N-terminal portion of an immunoglobulin chain. The fusion protein is produced in a recombinant system. A DNA sequence which encodes the amino acid sequence for the desired polypeptide is inserted into an expression vector for an immunoglobulin chain so that translation of the modified expression vector will result in a polypeptide comprising a leader sequence to direct secretion followed by the polypeptide corresponding to the recognition site and then the substantially complete immunoglobulin chain. This modified expression vector is introduced into a host cell that preferably has the capability of producing the other, complementary immunoglobulin chain, so that when the vector is translated, the host cell secretes a molecule corresponding to the complete immunoglobulin molecule with an extra peptide sequence corresponding to the recognition site attached to the N-terminus of one type of immunoglobulin chain. It is understood that the terms "immunoglobulin molecule" and "antibody" include fragments of the complete antibody protein, such as Fab and (Fab')₂.

The Polypeptide

Polypeptides which are contemplated by this aspect of the invention broadly include any polypeptide with an intrinsic three-dimensional structure that is maintained in a hydrophilic environment and that contains a site which recognizes a target molecule, where the amino terminal and carboxy terminal ends of the polypeptide are relatively accessible to the aqueous solvent. Preferred polypeptides correspond to the recognition domains of various receptors, such as CR1 and CR2, optionally cleaved to remove regions unnecessary to the recognition function and to leave accessible amino and carboxy terminals. The accessible ends of the polypeptide permit attachment to the leader sequence on the amino terminus and to the rest of the immunoglobulin chain on the carboxy terminus without disturbing the three-dimensional structure of the binding site.

Because the recognition polypeptide portion which is added to form the fusion protein of the present invention is added to the end of the immunoglobulin sequence, it does not displace elements contributing to the immunoglobulin structure. Therefore, it will not cause disruption of that structure. Consequently, any polypeptide capable of specific recognition may be used as the basis of the recognition or binding region incorporated into the fusion protein, so long as the polypeptide forms a discrete structure, stable in hydrophilic solution, with its amino and carboxy terminals accessible.

This invention is particularly suitable where the protein used as the basis of the recognition site is monovalent and the target molecule which binds to the recognition site has multiple binding sites. Where the $K_d$ of the monovalent binding reaction is 1 micromolar or higher, the antibodies of this invention, in which at least one chain of each arm of the antibody is a fusion protein containing an added binding site, are multivalent binding proteins which will bind with greater affinity (so that $K_d$ is less than 1 micromolar). For example, a soluble form of CR2 prepared without the transmembrane and cytoplasmic domains binds C3dg with $K_d$=27.5 micromolar (Moore, et al., 1989, supra), while a soluble fusion protein according to this invention based of CR2 binds with $K_d$=5 nM (Example 2, infra).

The polypeptide itself may optionally contain more than one binding or recognition site, so long as the polypeptide forms one or more discrete structures and the resultant fused protein is expressed and remains soluble. Preferably the size of the polypeptide will not make the fusion protein so large that its diffusion into animal tissues is unduly restricted.

Another preferred group of polypeptides are those made up of short consensus repeats (SCR), many of which are involved in the recognition of various complement fragments. Recognition or binding domains of these molecules are made up of a small number of SCRs. When a polypeptide is used whose sequence begins and ends with residues which are located between adjacent SCRs, the resulting polypeptide will have the desired properties of discrete three-dimensional structure and accessible termini. Thus, a polypeptide can be produced which has the desired binding site while it is substantially free of other peptide sequences which are unrelated to the recognition function. The group of proteins which are made up of short consensus repeats (SCR) includes the complement receptors CR1 and CR2 as well as C1r, C1s, factor B, C2, factor H, C4BP, DAF, MCP, C6, C7, interleukin 2 receptor alpha chain, beta-2-glycoprotein I, and factor XIII.

The polypeptides contemplated by this aspect of the invention are not limited to polypeptides composed of SCRs. They may be any desired three-dimensional peptide including, but not limited to, peptides containing desired epitopes, receptors of any kind including CD4, CD19, the T-cell receptor and the like, or molecular structures complementary to receptors, such as the C3dg recognition site.

The Immunoglobulin Chain

The fusion protein of this invention may be the result of joining the polypeptide to any immunoglobulin chain. The intact antibody molecule is stable in the circulatory system, and where the long-term stability of the fusion protein is important, it may be provided by the antibody portion of the fusion protein. The specificity of the antigen binding site is restricted only by the need for it not to interfere with the desired function of the fusion protein. In many circumstances, it may be desirable to use an antibody that is specific for an epitope that is not normally present in the animal. This invention, however, also contemplates employing antibodies specific to an epitope that is normally present in the animal. The specificity of the antigen binding site of the antibody may be chosen to facilitate purification of the fusion protein.

Immunoglobulin chains of different isotypes may be used. The preferred isotype will depend on the ultimate use of the recombinant fused protein. Gamma chains will direct the production of soluble fusion proteins which bind to Fc receptor; alpha chains will direct the production of fusion proteins which will bind to the intestinal wall; and epsilon chains will direct the production of fusion proteins which will bind to mast cells. Since the polypeptide recognition sequence may be attached to the N-terminus, which is part of the variable region of the immunoglobulin molecule, immunoglobulin fragments such as Fab and (Fab')$_2$ are also contemplated by this invention, so long as the variable region is present.

Fab or (Fab')$_2$ molecules can be produced by proteolytic cleavage or by the introduction of a stop codon after the hinge region in the heavy chain to delete the $F_C$ region. Depending upon the ultimate therapeutic use of the fusion protein, it may be preferable to maintain the $F_C$ region of a non-complement activating isotype in the immunoglobulin portion of the fusion protein to provide $F_C$ receptor-mediated clearance of the complement activating complexes.

The Expression System

The modified immunoglobulin expression vector can be constructed de novo, by combining a promoter, a leader sequence, the sequence corresponding to the desired polypeptide binding region, and the sequence of an immunoglobulin chain within a suitable vector. DNA sequences corresponding to these sequences may be obtained by a variety of well known methods including nucleic acid synthesis, amplification by polymerase chain reaction, and molecular cloning of genomic or cDNA. Promoter and leader sequences are readily available in the art for expression of a variety of proteins, including immunoglobulin chains. The available promoter and leader sequences may be used in any combination, so long as the promoter directs expression and the leader sequence directs secretion of the properly folded recombinant protein in the host system chosen for expression.

Suitable immunoglobulin chain sequences are also well known in the art. The sequence encoding the immunoglobulin chain is preferably provided in an expression vector which contains a promoter to direct expression and a leader sequence to direct secretion. Most preferably, an enhancer for expression is also included in the vector. Such expression vectors are readily available in the art. For example, a number of expression vectors encoding one or more immunoglobulin chains are available from the American Type Culture Collection, Rockville, Md.

A particularly preferred vector is the murine gamma-1 genomic clone designated pSNR021, which contains the sequence for the murine gamma-1 heavy chain specific for the hapten, 4-OH-3 nitrophenacetyl (NP), preceded by the native leader sequence directing secretion, under control of the immunoglobulin promoter, and containing an expression enhancer (Ballard, et al. (1986), *Proc. Natl. Acad. Sci. USA*, 83:9626–9630, which is incorporated herein by reference). Other vectors which provide for the expression and secretion of any one of the immunoglobulin chains will also function in the invention. Selection of the expression vector will further depend on the host cell used to express the modified vector, as the two must be compatible.

Effective methods for obtaining the desired DNA sequences for the polypeptide and the immunoglobulin chain are easily within the skill of the art, and a modified vector containing both the immunoglobulin sequence and the sequence corresponding to the desired recognition site can be prepared using any of the methods well known in the art. For example, a modified vector can be prepared by finding a restriction site in the sequence of the expression vector near the 5' end of the immunoglobulin chain and using that restriction site to construct an insertion site. The sequence for the insertion site is then inserted into the expression vector. The insertion site must be on the 3' side of the leader sequence which directs secretion.

Any of the standard methods for producing specific DNA sequences may be used to obtain a DNA sequence which will encode the desired polypeptide. In a preferred method, the known sequence of the corresponding protein is examined at the positions which will become the new amino and carboxy terminals of the polypeptide for sequences recognized by particular restriction enzymes. The desired DNA segment is then excised using these restriction enzymes, and the segment is cloned. Alternatively, the polymerase chain reaction (PCR) can be used to amplify the desired segment by designing primers which correspond to the ends of the segment as identified and include appropriate restriction sites for insertion and cloning.

Short oligonucleotides may be attached at one or both ends of the segment to facilitate expression of the desired fusion protein. Some added nucleotides may be necessary to retain the reading frame of both the polypeptide and the immunoglobulin chain, e.g., where the restriction sites do not correspond to the codons. The sequence of the modified expression vector must encode the cleavage signal for the leader peptide. In a preferred mode, codons for the first 1–10 amino acids of the immunoglobulin sequence are retained on the 5' side of the inserted sequence to ensure that the enzymes responsible for cleaving the leader peptide will recognize the cleavage site. Codons for these same amino acids may be repeated on the 3' side of the inserted sequence to ensure that the immunoglobulin portion of the finished molecule will fold properly.

Sequences encoding additional amino acids may be included between the 3' end of the polypeptide sequence and the 5' end of the immunoglobulin coding sequence to form a bridge between the two discrete structures. Such a bridge may provide additional flexibility to ensure that the expressed protein can fold properly without interference between the two discrete structure. The bridge can also contribute to the flexibility which permits spatial adaptation of the binding regions of the polypeptide sequences on the two arms of the antibody to the three-dimensional relationships of multiple binding sites on a target molecule.

The bridge peptide should be made up of a mixture of hydrophobic and hydrophilic amino acids which facilitate its function in aqueous solution, and which is resistant to proteases found in the mammalian circulatory system. Preferably, the bridge contains ten or fewer amino acids. A particularly preferred bridge is a dipeptide which consists of the amino acids valine and serine. While a bridge may provide benefits, its presence is not required so long as a proper reading frame is maintained and folding of the polypeptide or immunoglobulin portions are not affected by the other part of the fusion protein.

The DNA sequence encoding the polypeptide is inserted in the vector so that the polypeptide is attached to the N-terminal end of the immunoglobulin chain when the recombinant fusion protein is expressed. Most preferably the polypeptide, with or without bridge is fused to the first amino acid of the immunoglobulin sequence. More broadly it may be fused to any amino acid near the N-terminus, so long as the three-dimensional structure of the immunoglobulin chain is not disrupted upon expression.

Expression and Purification of the Recombinant Fusion Protein

The choice of a cell line in which the modified expression vector will be expressed is not critical. Generally, mammalian cell lines will be used because they express correctly folded immunoglobulin molecules, complete with any post-translational modifications that occur in vivo. Cell lines capable of expressing the vectors of this invention are readily available, see e.g., American Type Culture Collection. A preferred cell line is a myeloma that secretes the chain complementary to the chain encoded by the modified expression vector of this invention. Methods for producing such cells are taught in Schnee, et al. (1987), *Proc. Natl. Acad. Sci. USA*,84:6904–6908 which is incorporated herein by reference. A particularly useful cell line is a murine myeloma cell which is designated J558L and has been used by many different workers in the art (Ballard, et al. (1986); Bruggeman, et al. 1987); Gacoigne, et al. (1987); Oi, et al. (1983), *Proc. Natl. Acad. Sci. USA*, 80:825–829; Traunecker, et al. (1986), *Eur. J. Immunol.*, 16:851–854; Tsang, et al. (1988), *J. Immunol.*, 141:308–314; Williams, et al. (1986), *Gene*, 43:319–324)). This cell line produces immunoglobulin light (lambda) chain, but it has lost the ability to produce heavy chain.

Other cell lines which are suitable for use with expression vectors carrying different immunoglobulin sequences, or with promoter and/or leader sequences for different proteins or from different species, will be readily apparent to those of ordinary skill in the art. Prokaryotic host cells may be used to express the fusion proteins, for instance where the immunoglobulin sequence corresponds to a Fab fragment which does not include the Fc portion and therefore does not require post-translational glycosylation. (See Better, et al. (1987), *Science*, 240:1038–1041).

The modified expression vector which contains the sequence encoding the recombinant fusion protein can be introduced into the host cell by any of the techniques commonly used in the art, such as electroporation, lipofectoin and the like. Conditions under which the cells may be grown and the fusion protein expressed are characteristic of the particular host cells and promoters used and are well known in the art. Host cells containing the modified vector and expressing the complementary immunoglobulin chain will secrete the antibody molecule, correctly folded, with the polypeptide comprising the binding region fused to the N-terminal end of one of the chains. Where the host cell does not express either immunoglobulin chain, two modified vectors corresponding to the two types of immunoglobulin chain (heavy and light) and each carrying a polypeptide sequence encoding a different binding region, may be introduced into the cell. Such cells will secrete antibody molecules in which each arm has two different polypeptide binding regions attached to the two N-termini, respectively.

The recombinant fused protein can be recovered from the fermentation or culture broth in which the modified host cells are grown using standard techniques. Cells of the host can be removed by any convenient means, such as filtration. The fusion protein can be separated from the other components of the broth by standard biochemical separation means. A particularly useful method is affinity chromatography. The recombinant fusion protein carries a number of unique recognition sites: the antigen binding site of the original immunoglobulin, the recognition site inserted at the N-terminus, and other sites characteristic of the immunoglobulin molecule, such as the Fc sites. Affinity chromatography systems which contain moieties complementary to any of these can be used to purify the fusion protein by procedures which are well know to the ordinary worker. (*Methods in Enzymology*, Volume 34, edited by Jakoby, et al., Academic Press N.Y., 1974). In a preferred mode, the vector selected carries an immunoglobulin moiety specific for 4-hydroxy, 3-nitrophenacetyl, and affinity matrices which will bind the antigen binding site of the chimeric protein can be prepared as described by Bruggemann, et al. (1987) which is incorporated herein by reference.

Complement Receptor Analogs

In a preferred embodiment, the recombinant fusion protein of this invention comprises multiple polypeptide recognition sites based on SCRs having a complement binding region. Such binding regions generally have Kds less than or equal to one micromolar, which is much too low for use in the therapeutic methods described below. When polypeptides are attached to immunoglobulin chains, the antibody molecules produced by cells of this invention have at least two binding sites, because each arm of the antibody contains one chain from the modified vector encoding the polypeptide recognition site. Alternatively, the cell may contain two modified vectors encoding the light and heavy immunoglobulin chains respectively, where each chain has a recognition polypeptide attached to the N-terminal end. The polypeptides encoded by these vectors can be the same (in which case the antibody will carry four binding sites for the target molecule) or different (in which case the antibody will carry two sites each for two different target molecules).

Macromolecular constructs containing multiple complement binding sites and which have the same functional properties as the immunoglobulin fusion proteins are also contemplated by this invention. The macromolecular constructs comprise a plurality of peptides containing SCRs having complement binding sites attached to macromolecular, soluble, physiologically-acceptable carriers.

The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half-life for clearance. Suitable carriers include, but are not limited to, proteins such as serum albumin, heparin, or immunoglobulin, polymers such as polyethylene glycol or polyoxyethylated polyols, or proteins modified to reduce antigenicity by, for example, derivitizing with polyethylene glycol. Suitable carriers are known in the art and are described, for example, in U.S. Pat. Nos. 4,745,180, 4,766,106 and 4,847,325 and references cited therein.

The SCRs having complement binding sites are the same as those described above with respect to the immunoglobulin fusion protein except where chemical coupling to the macromolecular carrier is employed, the accessibility of the SCR peptide termini may not be required.

The constructs can be prepared in a number of ways. Where the carrier is a protein, the polypeptide may be attached by recombinant DNA methods, by inserting the DNA encoding the polypeptide sequence into an expression vector for the carrier, so that a fusion protein is expressed which contains multiple copies of the polypeptide attached to the carrier. SCR peptide joined to some portion of the immunoglobulin other than the N-terminus region is within this embodiment. The SCRs could be fused to another polypeptide with unique properties such as a CR1 derivative or other complement SCR containing protein derivatives including D1r, S1s, factor B, C2, factor H, C4BP, DAF, MCP, C6, C7, IL-2 receptor alpha, beta-2-glycoprotein 1 and factor XIII. Alternatively, the polypeptide can be produced separately for example by expression from an expression vector encoding a sequence for the polypeptide only or the polypeptide plus a coupling sequence (as taught, for example, in U.S. Pat. No. 4,894,443). Alternatively, the polypeptide may be obtained by proteolytic cleavage of the receptor protein, which leaves a polypeptide with the properties of discrete structure and complement binding sites contemplated by the invention. When the polypeptide is obtained separately it is subsequently coupled to the carrier macromolecule by chemical coupling techniques which are well known in the art.

Throughout the following discussion it is understood that the invention contemplates macromolecular constructs carrying a plurality of polypeptides comprising SCRs having complement binding sites as being substitutable for the recombinant fusion protein of the invention in a therapy described.

Therapeutic Use

Constructs can be prepared carrying binding sites for complement fragments corresponding to binding sites found on CR1 or CR2 or both. Constructs corresponding to CR2 bind to C3 fragments such as C3dg and iC3b or to EBV and the EBV-derived protein gp350/220. A monovalent CR2 molecule is not a preferred therapeutic agent, since its affinity for C3dg-coated gp350/220 is quite low. Multivalent CR2 molecules are preferred therapeutic agents, since their affinity for ligand is enhanced due to the valency. In Example 2, infra, the affinity of CR2-Ig, a two-arm construct based on an antibody and containing a bivalent receptor for C3dg and EBV, is 4000-fold and 10-fold higher than the affinity of monovalent receptor, respectively.

Complement binding sites of CR1 can form the basis of constructs binding to C3b (using the binding site of N-terminal SCRs of LHR-B or LHR-C), to C4b (using the binding site of the N-terminal SCRs of LHR-A) or to both. Where two modified expression vectors are used, one encoding the fusion protein based on immunoglobulin light chain with the binding region of one complement receptor site attached and the other encoding a fusion protein based on the heavy chain with the binding region of the other complement receptor site attached, a construct may be obtained that binds to both C3b and C4b. Transfection of a myeloma cell which does not secrete antibody with both of these vectors will result in secretion of an antibody which has two sites for C3b and two sites for C4b. Alternatively, SCRs containing C3b and C4b binding sites can be attached to the N-terminus of the immunoglobulin heavy chain in tandem to produce an antibody that also has two sites for C3b and two sites for C4b and should behind both C3b and C4b.

While soluble complement binding protein based on CR1 has been prepared (Fearon, et al., 1989), constructs prepared according to the present invention will have enhanced stability in the mammalian circulatory system based on the stability of the carrier portion of the construct. The half-life of immunoglobulin fusion proteins containing sites from either complement receptor will benefit from the half-life of the parent immunologbulin, which as been determined to be 6–8 days (Vieira, et al. (1988), *Eur. J. Immunol.,* 18:313–316). Where the therapeutic use of the construct is the inhibition of complement activation, the serum half-life of the construct desirably is at least about an hour. Where the construct is used in anti-viral or anti-immune therapy, the serum half-life of the construct desirably is at least about ten hours and preferably at least about a day. Half-life can readily be measured by routine pharmokinetic techniques known in the art.

A CR1 immunoglobulin chimera of the present invention was constructed that contained SCRs 8 through 11 of the CR1 sequence (corresponding to a C3b binding domain) attached to the NH2-terminal region of the immunoglobulin heavy chain. This construct maintained the alternative pathway function activity of sCR1/pBSCR1c that is mediated through C3b binding and also retained the in vivo stability characteristic of the immunoglobulin portion of the chimera. The in vivo characteristics conferred by the immunoglobulin make such a construct a preferred therapeutic molecule for the treatment of CR1 related diseases or disorders. Such diseases or disorders include but are not limited to diseases involving inappropriate or undesirable complement activation (such as hemodialysis disorders, hyperacute allograft and xenograft rejection, interleukin-2 (IL-2) induced toxicity during IL-2 therapy, hematologic malignancies such as AIDS), infections (such as lepromatus leprosy, AIDS, and sepsis); inflammation disorders (such a those present in autoimmune diseases, adult respiratory distress syndrome, Crohn's disease, thermal injury, burns, and frostbite); immune complex disorders (such as in autoimmune diseases, rheumatoid arthritis, systemic lupus erythematosus, proliferative nephritis, glomerulonephritis, hemolytic anemia, and myasthenia gravis); neurological disorders (such as multiple scierosis, Gullain Barre Syndrome, stroke, traumatic brain injury and Parkinson's disease); and post ischemic reperfusion conditions (such as myocardial infarct, balloon angioplasty, and post pump syndrome in cardiopulmonary bypass).

Knowledge of the biological roe of CR2 in the immune response is sufficient to indicate that the potential exists for a positive feedback loop in which excessive complement activation by immune complexes leads to further activation of B-cells leading to additional generation of autoantibodies that form more immune complexes. A soluble CR2 that competes with the cellular receptor for the C3dg-containing complexes could block this positive feedback loop to B cell activation by complement.

Soluble constructs carrying complement binding sites may be used in the treatment of a number of disease conditions related to complement-dependent cellular activation, where administration of said constructs will inhibit activation of complement and the complement-dependent activation of cells. Such disease conditions include but are not limited to autoantibody immune complex diseases (such as idiopathic thrombocytopenia purpera, systemic lupus erythematosus, myasthenia gravis, arthritis, autoimmune hemolysis, glomerulonephritis, multiple sclerosis, Pemphigus vulgaris, cryoglobulinemia, and AIDS) Epstein Barr virus associated diseases (such as Sjogren's Symdrome, rheumatoid arthritis, Burkitt's lymphoma, Hodgkins disease, virus (AIDS or EBV) associated B cell lymphoma, chronic fatigue syndrome, parasitic diseases such as Leishmania and immunosuppressed disease states (such as viral infection following allograft transplantation or AIDS).

EBV binds to CR2 on B-cells as a critical step in infection by the virus. C3dg complexes with antigen and binds to the CR2 receptor on B-cells to activate antibody production. Phagocytosis is triggered by iC3b binding to CR3 on neutrophilis and macrophages. During inflammation, iC3b binds to CR3 on neutrophilis, promoting adherence to endothelial cells. During inflammation C3b and C4b bind to a variety of cell types via cell-bound CR1.

Constructs containing CR2, such as CR2-Ig, will compete with cell-bound CR2 for EBV, reducing binding of EBV to cells and inhibiting EBV infection. Such constructs will compete for C3dg and thereby inhibit B-cell activation. This effect is particularly important in autoimmune diseases such as rheumatoid arthritis and systemic lupus erythematosus. By binding to iC3b, the constructs can inhibit phagocytosis by neutrophilis and macrophages. The constructs can also serve to reduce inflammation.

A CR2-immunoglobulin chimera of the present invention was constructed that contained SCRs 1 and 2 of CR2 attached to the N-terminus of the immunoglobulin heavy chain. This chimeric molecule demonstrated immunosupression in vivo of both T-dependent and T-independent immune responses and identified CR2 as the complement receptor that mediates the capacity of C3 t enhance the immune response. This finding provides an in vivo correlate for many studies suggesting a role for CR2 in B cell activation in vitro and clarifies the previous observation that a monoclonal antibody to murine CR1 that was cross-reactive with CR2 inhibited the antibody response in mice. In conjunction with the demonstration that CR2 is a ligand binding subunit of the CD19/CR2 complex, the immunosuppressive effect of the CR2-IgG1 provides the first evidence that the signal transducing function of the CD19/CR2 complex has the biological consequence of potentiating the response of B cells to antigen in vivo. Because the soluble CR2-IgG1 chimera was able to inhibit the in vivo response of B cells to antigen, it should be useful therapeutically for treating those diseases or disorders exhibiting inappropriate or undesirable B cell activation. In addition to the disease or disorders listed above, such chimeras should be useful in preventing the undesirable primary antibody responses to immunotherapeutic agents, such as xenogenic monoclonal antibodies, used for immunosuppression (following allograft transplantation, for example) or for cancer therapy.

A construct whose binding regions are based on CR1 sequences, will have complement inhibitory functions comparable to that of soluble CR1, including reducing tissue damage associated with ischemia in myocardial infarct and other disorders involving undesirable complement activity, but the construct will have a longer half-life in vivo than soluble CR1 and preferably a greater capacity to diffuse into tissue sites of inflammation.

Complement activating parasites, bacteria and yeasts, (i.e., leishmania, haemophilus) use CR3 to enter a cell and start a multiplicative cycle. A construct carrying a complement receptor recognition sequence will mask the receptor binding sites on the parasites, and reroute the complexes to Fc receptors via the Fc domain of the gamma-1 chain of the fusion protein. Thus the parasites will be exposed to a Fc-receptor-triggered oxidative burst rather than being taken up into neutrophilis by CR3-mediated phagocytosis, where they are protected from the animal's defense mechanisms.

Treatment of animals to inhibit the various complement-dependent phenomena may be accomplished by administration of the recombinant fused proteins or constructs provided by this invention. Recombinant immunoglobulin fusion proteins carrying recognition peptides which bind to target molecules other than complement are used therapeutically to inhibit cellular phenomena dependent on binding of their respective target molecules to the cells.

In the above method, the compounds may be administered by any convenient route, for example by infusion or bolus injection. Various delivery systems are known and can be used for deliver of fusion proteins and constructs. These include encapsulation in liposomes, microparticles, or microcapsules. Other methods of introduction include but are not limited to intradermal, intramuscular, intrapertioneal, intravenous, subcutaneous, intranasal, and oral routes.

The present invention also provides pharmaceutical compositions. Such compositions comprise a therapeutically effective amount of a fusion protein or construct and a pharmaceutically acceptable vehicle. Such a vehicle includes but is not limited to saline, buffered saline, dextrose, and water.

Typically compositions for intravenous administration are solutions in sterile isotonic aqueous buffer. Where necessary, the composition may also include a solubilizing agent and a local anaesthetic such as lignocaine to ease pain at the site of the injection. Generally, the ingredients will be supplied either separately or mixed together in unit dosage form, contained in a hermetically sealed container such as an ampoule or sachette indicating the quantity of active agent in activity units. Where the composition is to be administered by infusion, it can be dispensed with an infusion bottle containing sterile pharmaceutical grade 'Water for Injection' or saline. Where the composition is to be administered by injection, an ampoule of sterile water for injection or saline may be provided so that the ingredients may be mixed prior to administration.

A pharmaceutical pack comprising one or more containers filled with one or more of the ingredients of the pharmaceutical composition is also within the scope of the invention.

The composition will be administered to maintain plasma levels of the protein in the range of from about 1 to about 100 ug/ml, based on the Kd for the specific binding reactions of the fusion protein or construct.

The following examples are included for illustrative purposes only and are not intended to limit the scope of the invention.

EXAMPLE 1

The human complement receptor type 2 (CR2, CD21) is the ligand for human C3dg and the Epstein-Barr-Virus (EBV). The binding sites for these two ligands have ben localized to the two amino-terminal short consensus repeats (SCR) (Lowell, et al., (1980), *J. Exp. Med.*, 170:1931–1946). These SCRs were cloned onto the 5' end of murine genomic heavy chain DNA, coding for a gamma-1 chain (FIG. 1). The resulting fusion protein was successfully expressed in a murine myeloma cell line and is designated CR2-IgG1.

Cloning of CR2 into Murine Genomic Gamma-1 DNA

Figure 3:
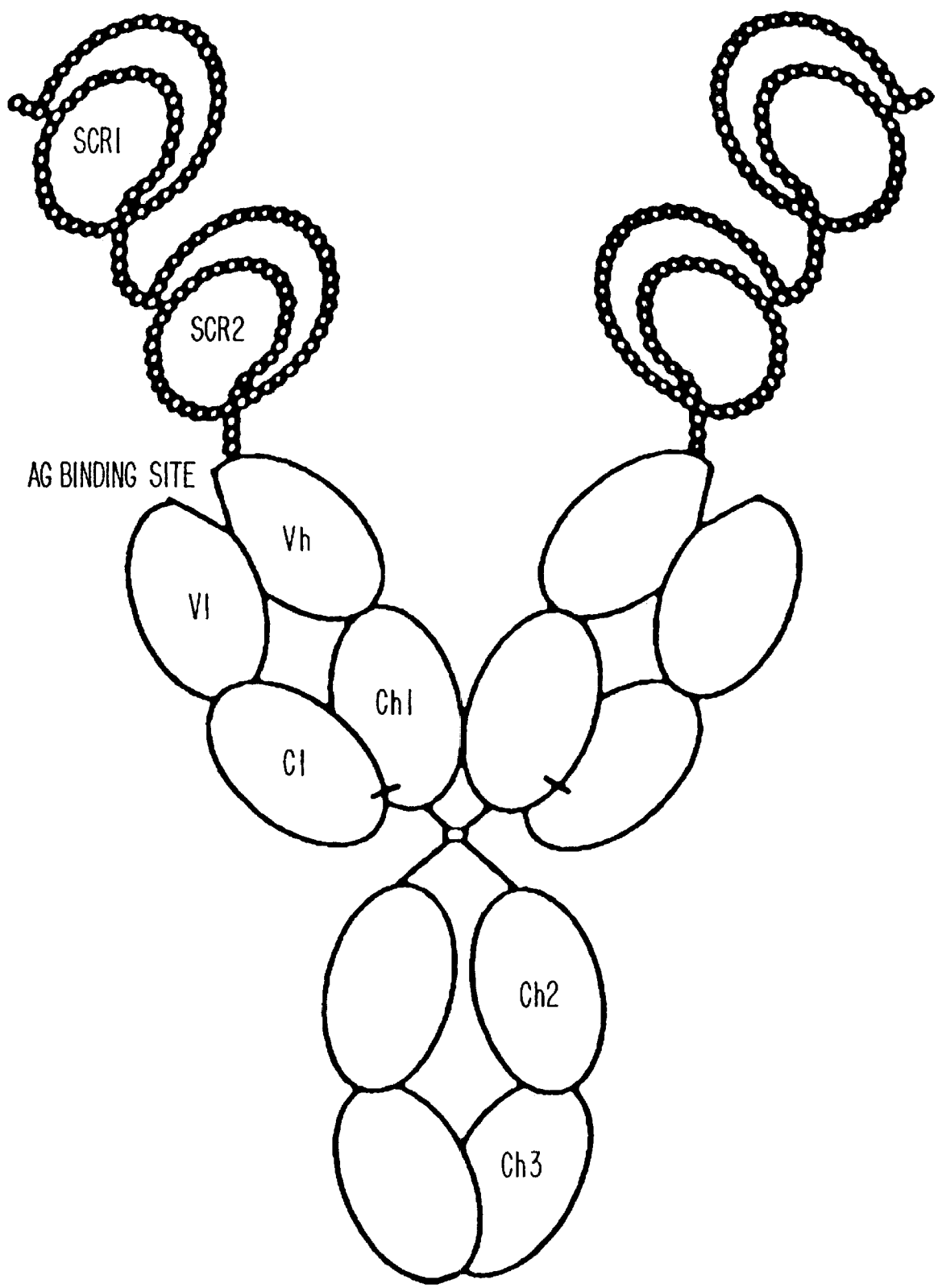
FIG. 3. Conceptual model of the complete CR2-IgG1. SCR1,2: short consensus repeats of the CR2 molecule; Vh, Chl, h2, h3: variable and constant domains of the heavy chain; V1C1: variable and constant domains of the lambda light chain.

A murine gamma-1 genomic clone designated pSNR021 according to Ballard, et al. (1986), *Proc. Natl. Acad. Sci. USA*, 83:9626–9630 (mutant 1 in the reference) contains a PstI site between amino acid 5 and 6, and it confers G418 resistance upon stable host integration. An EaeI-XhoI fragment containing the first two SCRs of CR2 was isolated from the cDNA clone (based on the sequence of Weis, et al. (1988), *J. Exp. Med.*, 167:1047–1066). Two short oligonucleotides were constructed to enable insertion of the CR2 fragment into the gamma-1 DNA at the PstI site. The 5' oligonucleotide served to maintain the reading frame of the immunoglobulin. The 3' oligonucleotide encoded a valine and serine to provide a flexible connection between CR2 and VH chain (see sequences in FIG. 2). The resulting clone (pSNRCR2) coded for a murine gamma-1 chain starting again with amino acids 1–5 (FIGS. 1, 2, 3).

Electroporation and Selection

The J558L myeloma cell line was kindly provided by Dr. S. L. Morrison. It was maintained in RPMI 1640 medium ("ATCC Catalog of Cell Lines and Hybridomas," 6th Ed., 1988, pp. 353–4) supplemented with 9% (v/v) bovine calf serum (BCS). J558L is a heavy chain-loss variant of J558 (ATCC Accession # TIB 6) that synthesizes lambda light chains. pSNRCR2 and an unmodified gamma-1 DNA (pSNR021) were linearized with Pvu I. Myeloma cells were transfected by electroporation and selected after 24 hr by addition of G418 (1 mg/ml) and cloned in microtiter plates.

The resulting clones were picked and the supernatants assayed for IgG1 reactivity in an ELISA. This was performed as follows:

Antibody directed to the Fc-fragments of murine IgG was immobilized to the wells of microtiter plates, which would capture any IgG1 present in the tissue culture supernatants Binding of a second antibody specific for the lambda light chain of murine immunoglobulins and labeled with peroxidase then signaled the presence of an intact IgG containing the gamma-1 chain contributed by the plasmid and the lambda chain derived from the parent myeloma cell.

Purification of Proteins

Figure 9:
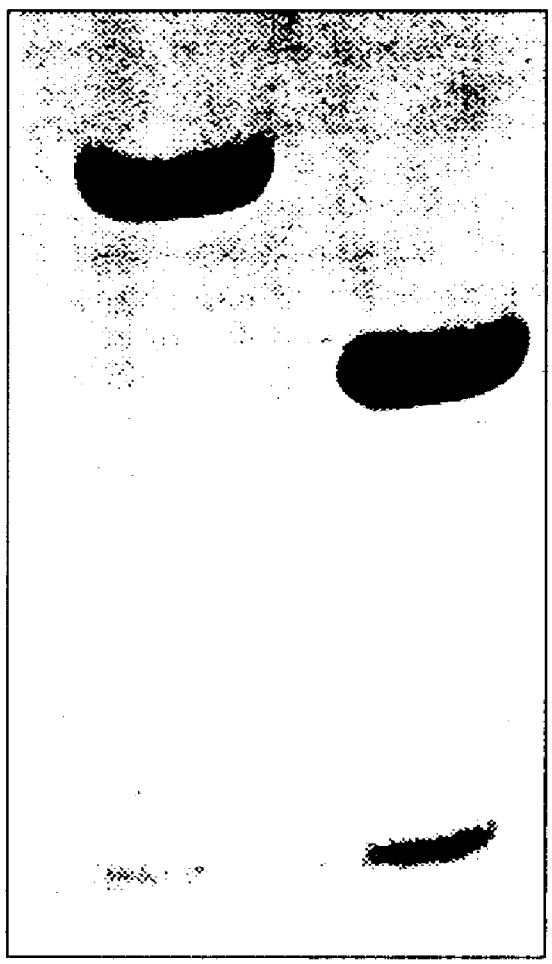
FIG. 9. SDS-polyacrylamide gels of purified, recombinant CR2-IgG1 (left lane) and IgG1 (right lane) secreted by J558L cells stably expressing the PSNRCR2 and pSNR021* plasmids, respectively.

The expressed proteins CR2-IgG1 and IgG1 were purified from culture supernatants by affinity chromatography on NIP-sepharose as published (Bruggemann, et al. (1987), *J. Exp. Med.*, 166:1351–1361). Analysis of the purified proteins by SDS-PAGE showed that the light chains were identical in size, and that the heavy chain of the CR2-IgG1 chimera was 19 kD larger than that of IgG1, consistent with the presence of the two SCRs with two potential N-glycosylation sites. See FIG. 9.

EXAMPLE 2

Binding Assays Competition of Constructs with Cellbound CR2 for Human C3dg

K562 cells (ATCC Accession No. CLL 243) were transfected with an expression vector containing the sequence of human CR2 prepared according to Lowell, et al. (1989) using lipofection (Bethesda Research Laboratories, Inc.). Glutaraldehyde polymerized C3dg was labeled with $^{125}$I (pC3dg) (Carter, et al., *J. Immunol.*, 143:1755–1760). Cells were incubated with 1 ug/ml of pC3dg in the presence or absence of incremental concentrations of IgG1 or CR2-IgG1 from Example 1 for 30' on ice and centrifuged through a mixture of equal parts of dibutyl- and dinonylphthalate. The radioactivity in pellet and supernatant was determined in a gamma-counter.

Figure 4:
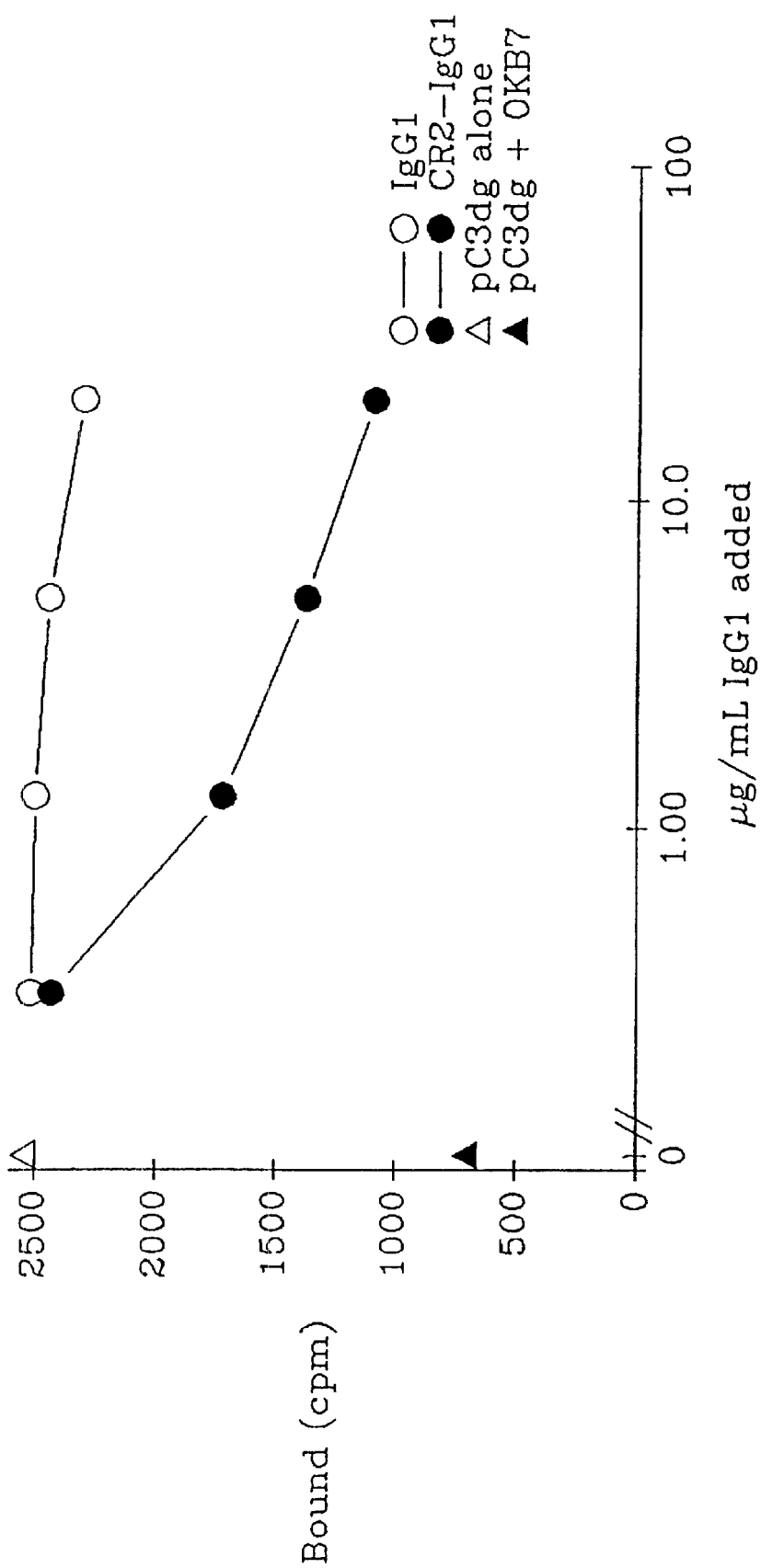
FIG. 4. Binding of $^{125}$I-labeled pC3dg to CR2 of K562 cells is inhibited by CR2-IgG1.

The interaction of polymeric C3dg with CR2 on K562 cells cold be inhibited by recombinant soluble CR2-IgG1, with 50% inhibition being achieved at a concentration of 5 nM (FIG. 4). Monovalent binding of C3dg to a soluble, truncated form of CR2 lacking the transmembrane and cytoplasmic domain occurs with Kd of 27.5 uM (Moore, et al., (1989)). Therefore, the two CR2 binding domains in the two arms of the chimeric protein interact with pC3dg to create a bivalent binding reaction and substantially enhance affinity.

Binding of CR2-IgG1 to Cell-Bound EBV Proteins

B95/8 cells (ATCC Accession # CRL 1612) were grown in the same medium used in Example 1 but with 40 ng/ml PMA (phorbol myristate acetate) added to induce expression and secretion of EBV as described in Dolyniuk, et al. (1976) *J. Virol.*, 17:935–949.

IgG1 and CR2-IgG1 were labelled with $^{125}$I to specific activities of $2.67 \times 10^6$/mg and $2.37 \times 10^6$/mg (Fraker, et al., (1978) *Biochem. Biophys. Res. Comm.*, 80:849–857). Viable cells from a culture of induced B95/8 were banded on Ficoll-Paque (Pharmacia). Cells were incubated with ligands for 30' on ice and centrifuged through a mixture of equal parts of dibutyl- and dinomylphthalate. The radioactivity in pellet and supernatant was determined in a gamma-counter.

Figure 5:
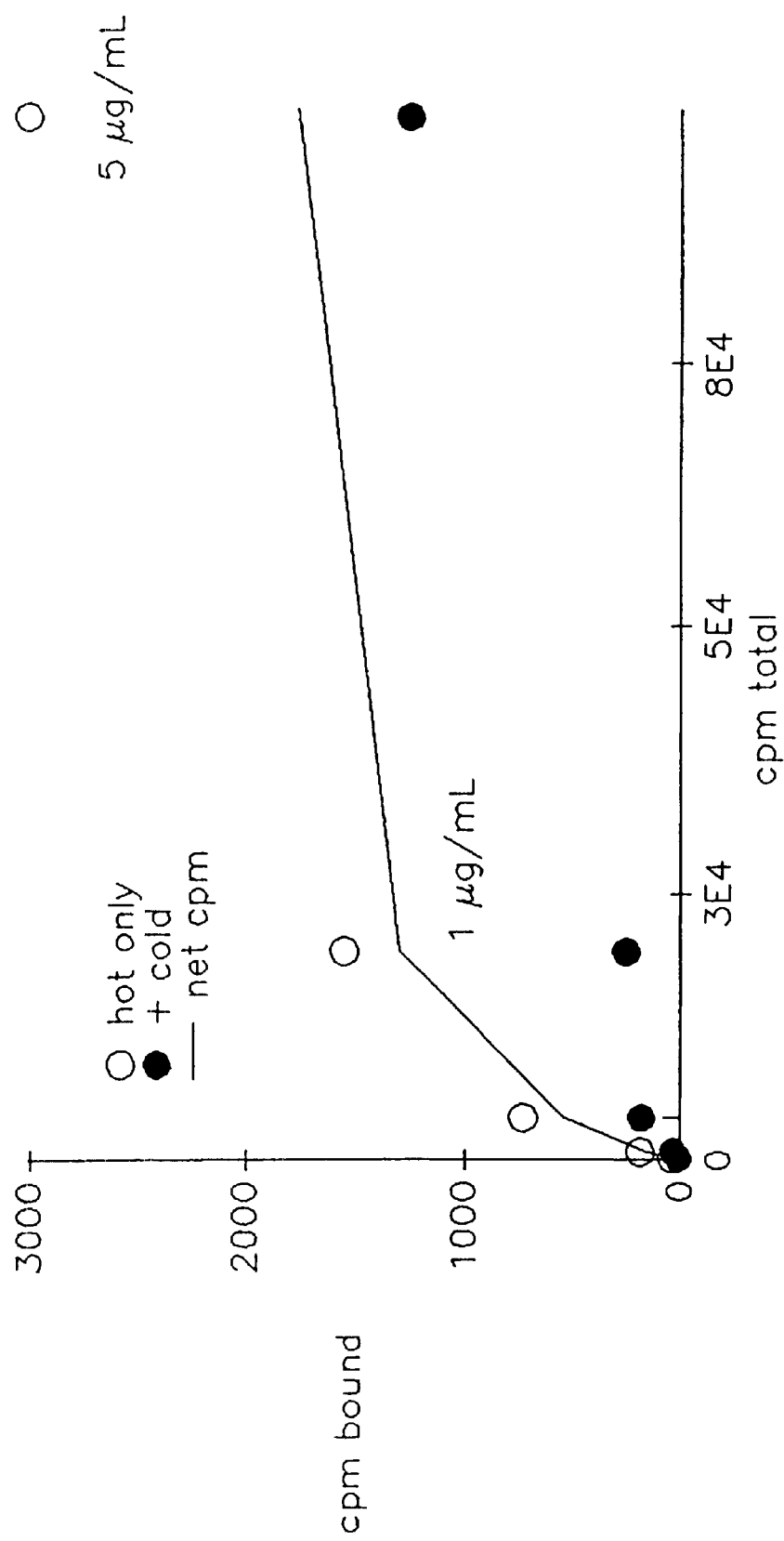
FIG. 5. Binding of $^{125}$I-labeled CR2-IgG1 to B95/8 cells in the presence or absence of 30-fold molar excess of unlabeled competitor.

Radiolabeled CR2-IgG1 bound to EBV proteins expressed on B95/8 cells with an affinity of 0.5 nM (FIG. 5). This again indicates divalent interaction of CR2 with EBV, as the Kd for monovalent binding is 3.2 nM (Moore, et al., 1989).

Uptake of CR2-IgG1 Construct by Particles Coated with Mouse or Human Serum

The interaction of CR2-IgG1 with urine and human C3 fragments was compared by assaying the uptake of the $^{125}$I-labeled chimera to zymosan particles that had been incubated in mouse and human serum, respectively, in the presence of $Mg^{2+}$ and $Ca^{2+}$, which permits the activation of the alternative pathway, or in the presence of EDTA which blocks complement activation. These complement-activating particles are coated primarily with the C3b and iC3b fragments of C3, and the latter, which contain the C3dg region, bind to the same site in CR2 and with the same affinity as does C3dg.

Figure 10B:
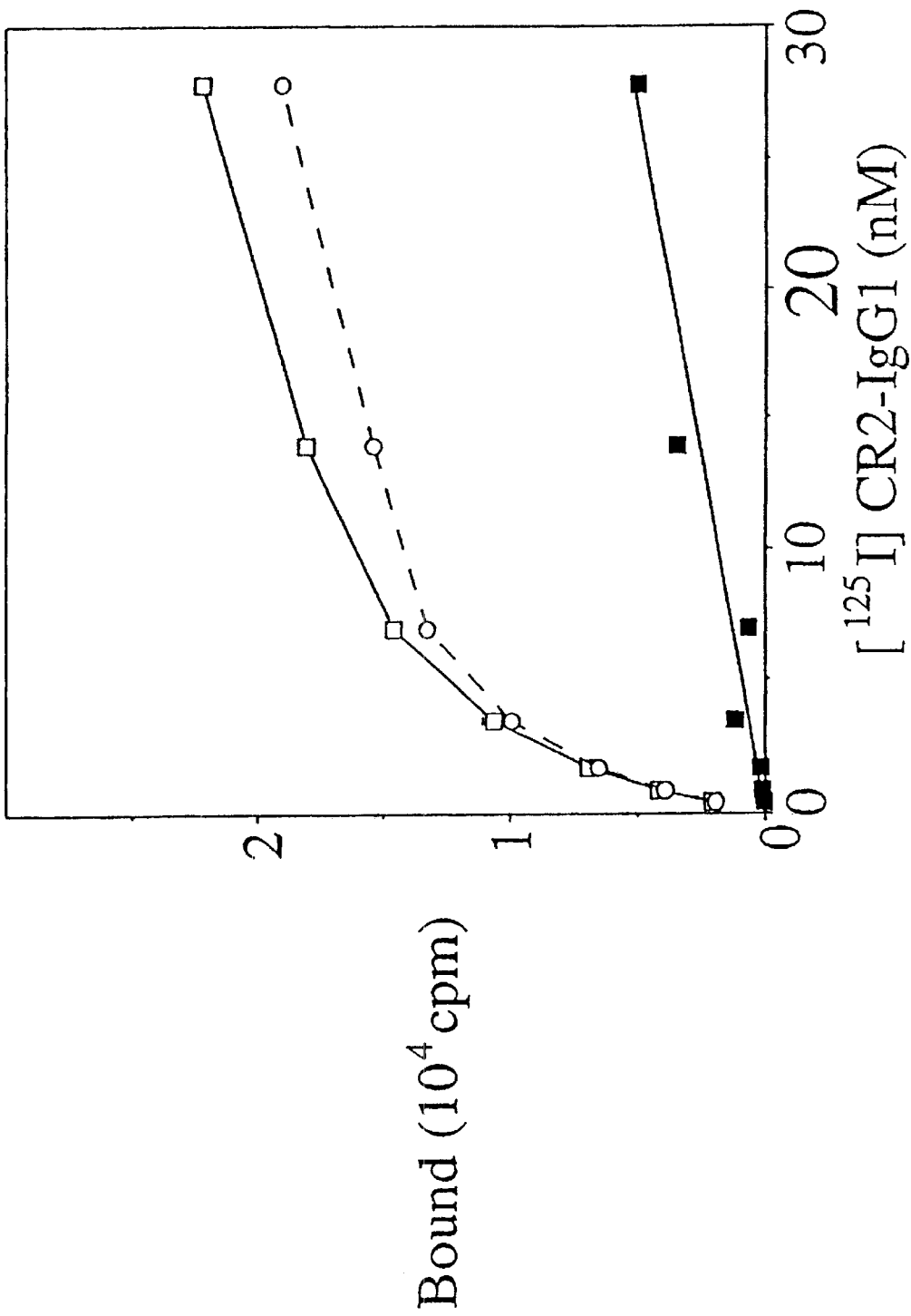
Figure 11A:
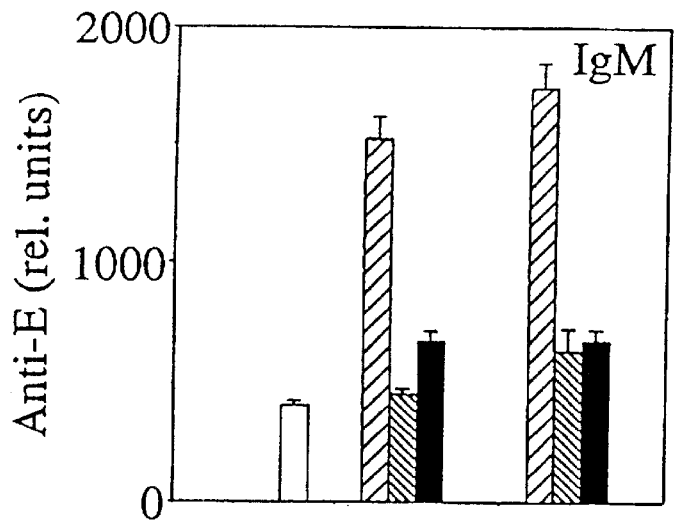
FIGS. 11A–11F. Comparison of the immunosuppressive effects of CR2-IgG1 and cobra venom factor (CVF) in mice immunized with sheep erythrocytes (E). One group of eight female BALB/c mice between six and eight weeks of age was depleted of C3 by pretreatment with four doses of 5 microgram of CVF (kindly provided by Dr. O. Gotze, Gottingen, FRG) 24 hours prior to intravenous immunization with 4×10⁵ or 4×10⁶ E. Two groups of mice received intravenously a total of 800micrograms of CR2-IgG1 or IgG1 in four equally divided doses during the first 24 hours after immunization. A fourth group of mice received only PBS and was not immunized. On day 5, the number of splenic anti-sheep E plaque-forming cells was assayed and the serum concentrations of specific anti-sheep E in five isotypes was measured by ELISA. The data represent mean +/− SEM of 4 mice for each determination.
Figure 11B:
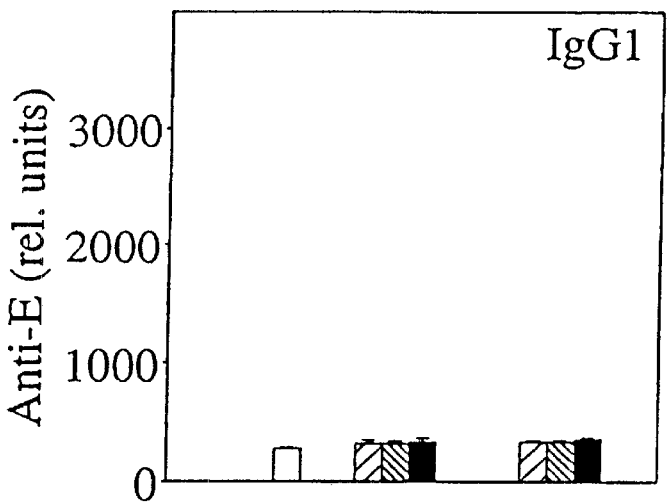
Figure 11C:
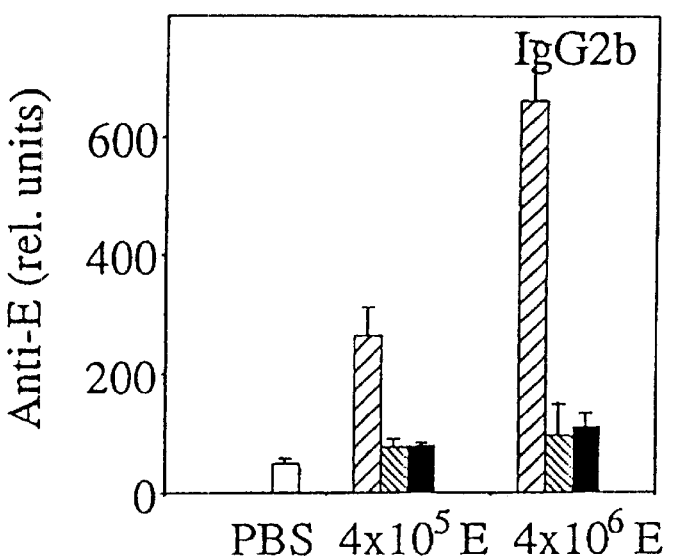
Figure 11D:
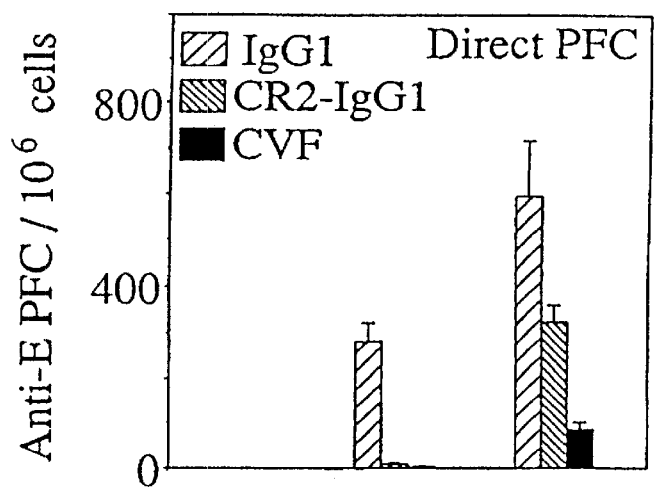
Figure 11E:
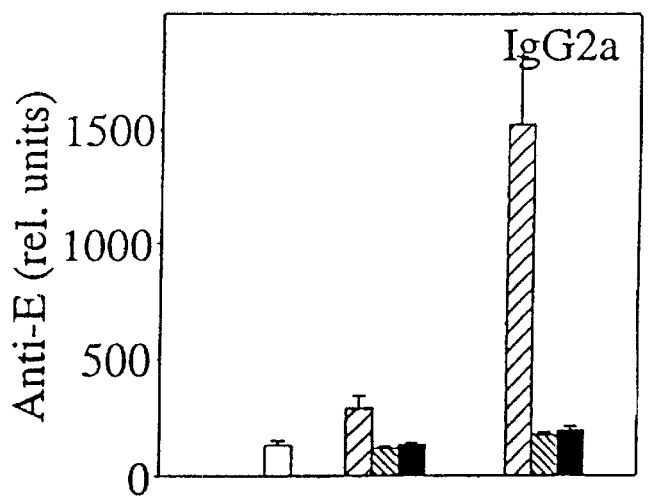
Figure 11F:
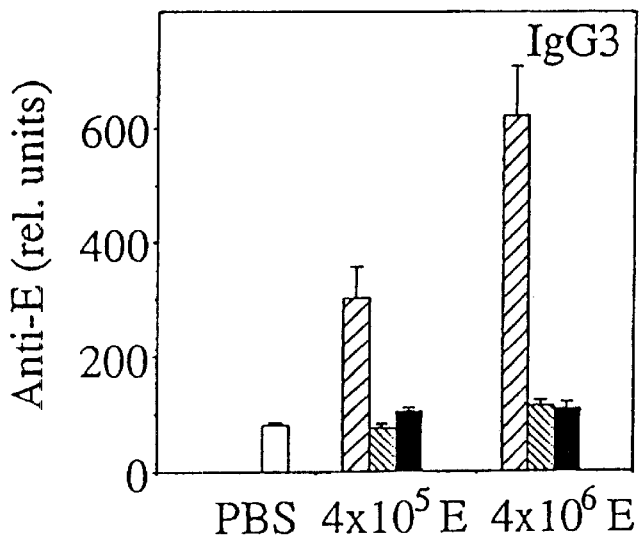
Figure 12A:
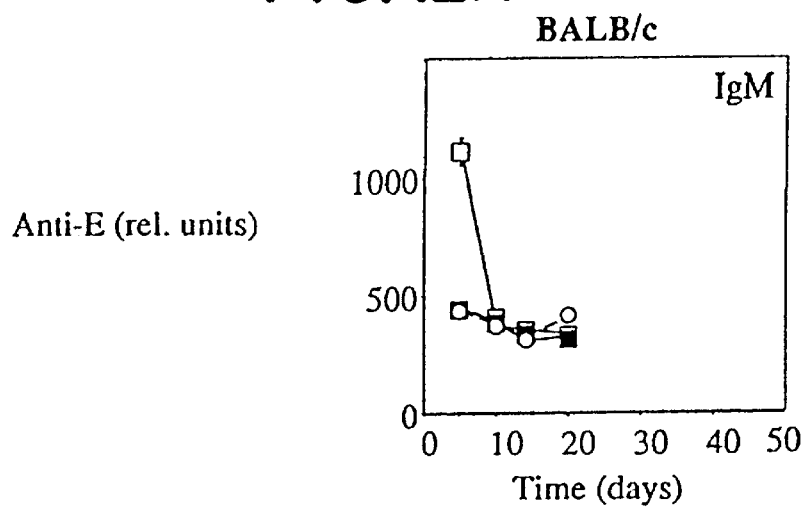
FIGS. 12A–12J. Prolonged suppression by CR2-IgG1 of the antibody response to sheep E in BALB/c and C3H/HeJ mice. Two groups of six BALB/c and C3H/HeJ mice, respectively, were administered a total of 800 micrograms CR2-IgG1 (filled square) or IgG1 (open square) in divided doses immediately prior to, during and up to 17 hr after immunization with 4×10⁶ sheep E. A third group received only PBS and was not immunized (open circle). Specific antibody concentrations were determined by ELISA every five days. Data represent mean +/− SEM of the results of the four mice remaining after excluding the highest and lowest responders.
Figure 12B:
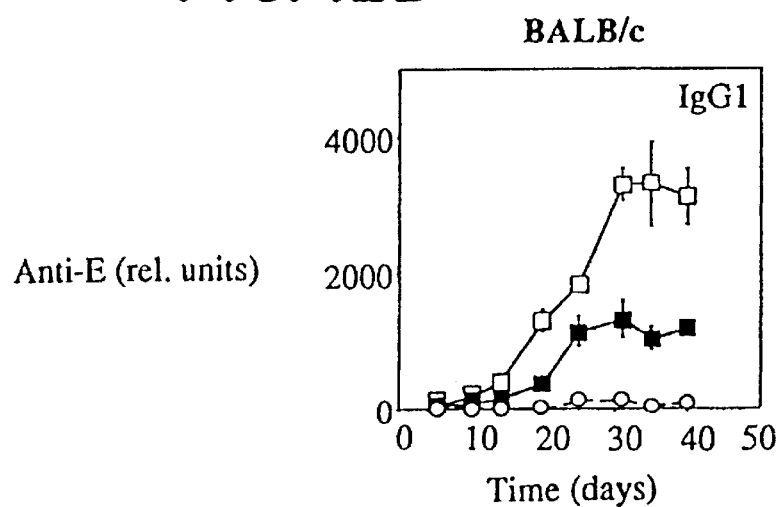
Figure 12C:
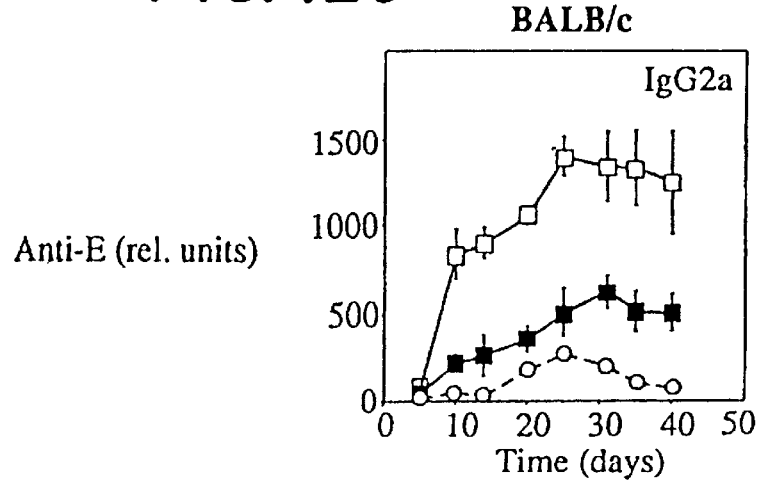
Figure 12D:
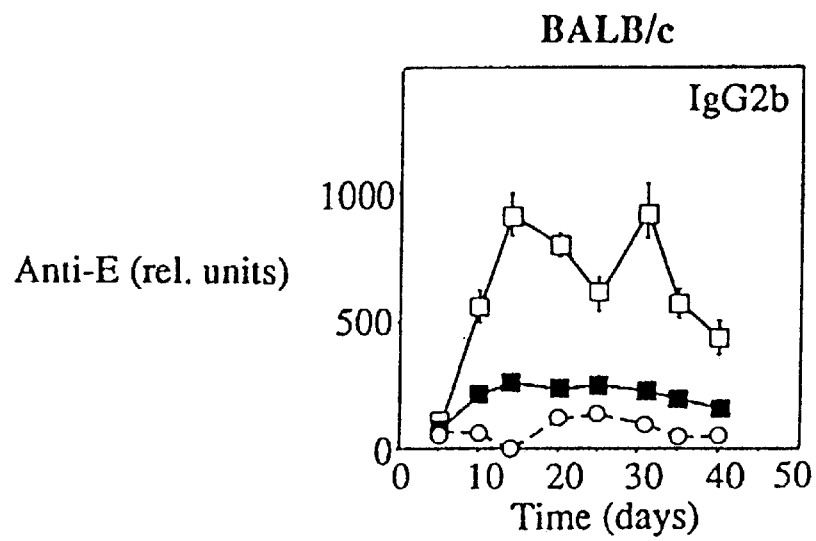
Figure 12E:
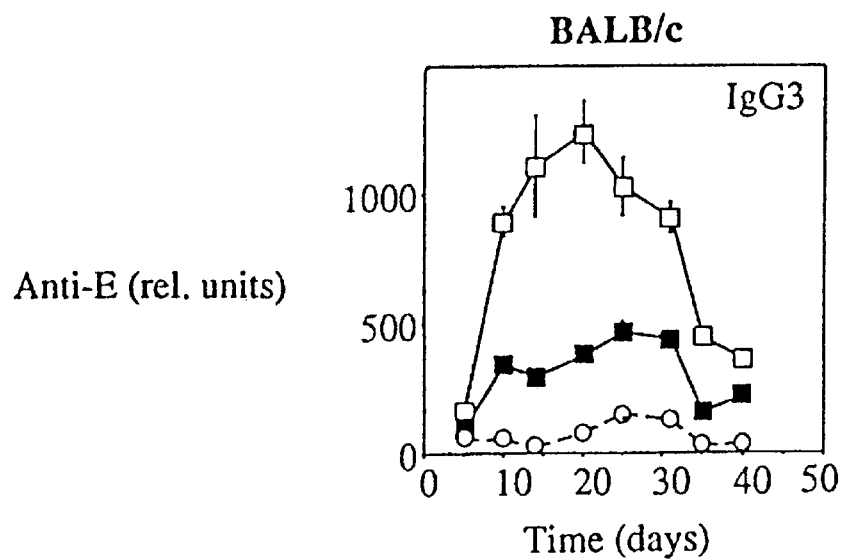
Figure 12F:
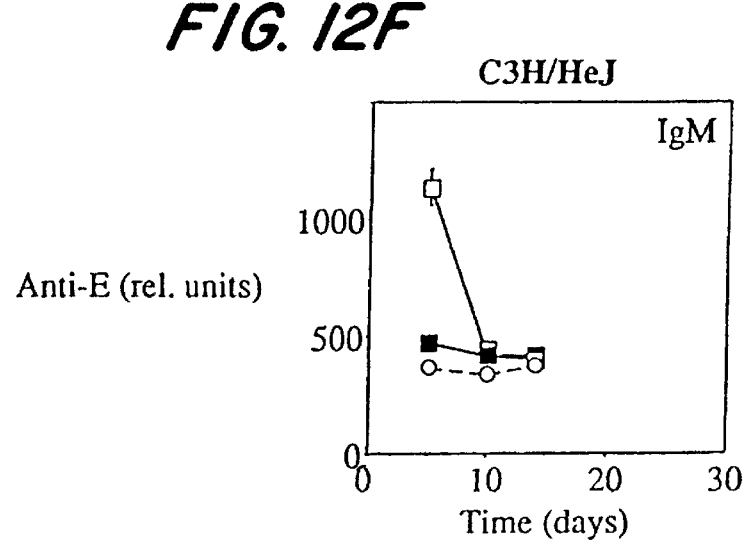
Figure 12G:
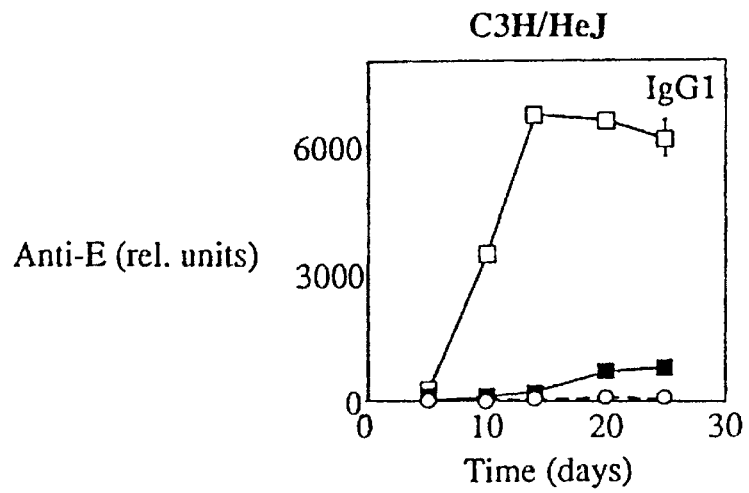
Figure 12H:
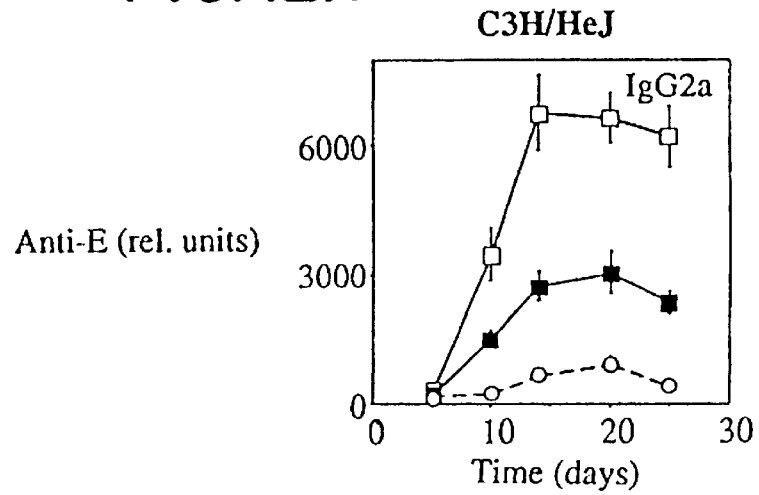
Figure 12I:
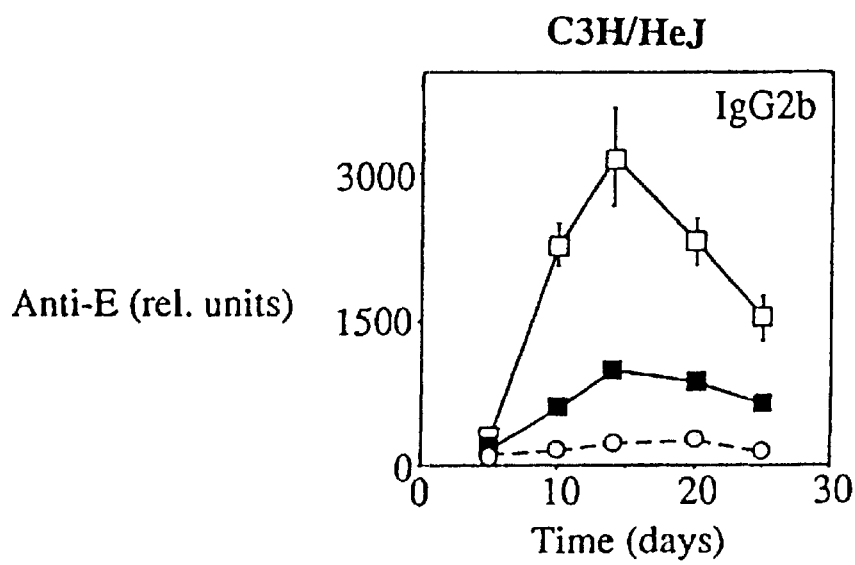
Figure 12J:
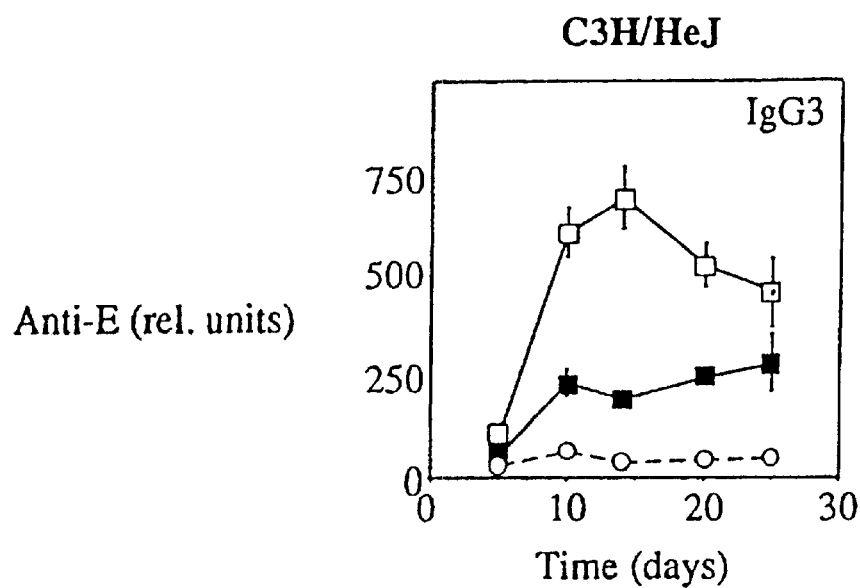

The CR2-IgG1 bound to zymosan particles that had been coated with human and mouse C3 fragments with Kd's of 10.0+/−3.7 nM (n=5, mean +/− SD) and 3.2+/−1.6 nM (n=4), respectively, indicating that the chimera has an even higher affinity for the heterologous than the homologous ligand. (See FIG. 10.) Therefore, the CR2-IgG1 chimera can be used to compete with cellular CR2 for the binding of complement-activating complexes in the mouse.

EXAMPLE 3

Inhibition of EBV-Infection

EBV was purified from cells grown according to Example 2. The EBV was pelleted from the supernatant by centrifugation at 12000 $g_{avg}$ for 90', resuspended in 1% of the original volume and filtered through a 0.8 um membrane filter to give 100X EBV. $5\times10^4$ RAMOS cells (ATCC Accession # 1596) from a culture in log phase were incubated in 90 ul of the tissue culture medium of Example 2 with 10 ul of 100X EBV and various concentrations of CR2-IgG1 or the IgG1 control from Example 1. After 2 days incubation at 37° C. the cells were washed, layered on microscope slices, air-dried and methanol fixed. They were stained by sequential incubation for 30' at 37° C. with 10% of a human serum that had been shown to contain antibodies for Epstein-Barr nuclear antigen (EBNA) and goat anti-human C3-FITC. (Gerber (1980), "Herpesvirus," in Lennette, et al., eds. Manual of Clinical Microbiology 3rd ed., *Am. Soc. Microbiol.*, Washington, pp. 807–809).

Infection of RAMOS cells with EBV could be inhibited in a dose-dependent manner by the addition of CR2-IgG1. At a concentration of 0.4 ug/ml of EBNA expression was reduced to background levels. Control IgG1 had the same effect as no addition; in either case 10% of the RAMOS cells were infected.

EXAMPLE 4

Inhibiting EBV-Induced $^3$H-Thymidine Incorporation by PBL

The capacity of CR2-IgG1 to inhibit EBV-induced proliferation of PBLs was assessed in the presence of cyclosporin, which prevented the growth of T-lymphocytes. The EBV virus was purified from the supernatant of 8 day cultures grown as describe din Example 2. Cells were removed by centrifugation at 3500 $g_{avg}$ for 15'. The supernatant was passed through an 0.4 um membrane filter and used for infection of peripheral blood leukocytes (PBL). Mononuclear lymphocytes were isolated from peripheral blood by centrifugation on Ficoll-Paque. $10^5$ PBL in 50 ul RPMI 1640, 20% BCS were incubated with 50 ul of EBV suspension and various concentrations of CR2-IgG1 or the IgG1 control from Example 1 overnight at 37°. To avoid interferences by T cells, cyclosporin (2 ug/ml) was then added from a 1 mg/ml stock in RPMI 1640, 10% ethanol, 2% Tween 80 (Rickinson, et al., *Cell Immunol.* (1984), vol. 87, pp. 646–658). After 48 h, 1 uCi of $^3$H-thymidine was added. Twelve hours later the cells were harvested, and the incorporated radioactivity was determined by liquid scintillation counting.

Figure 6:
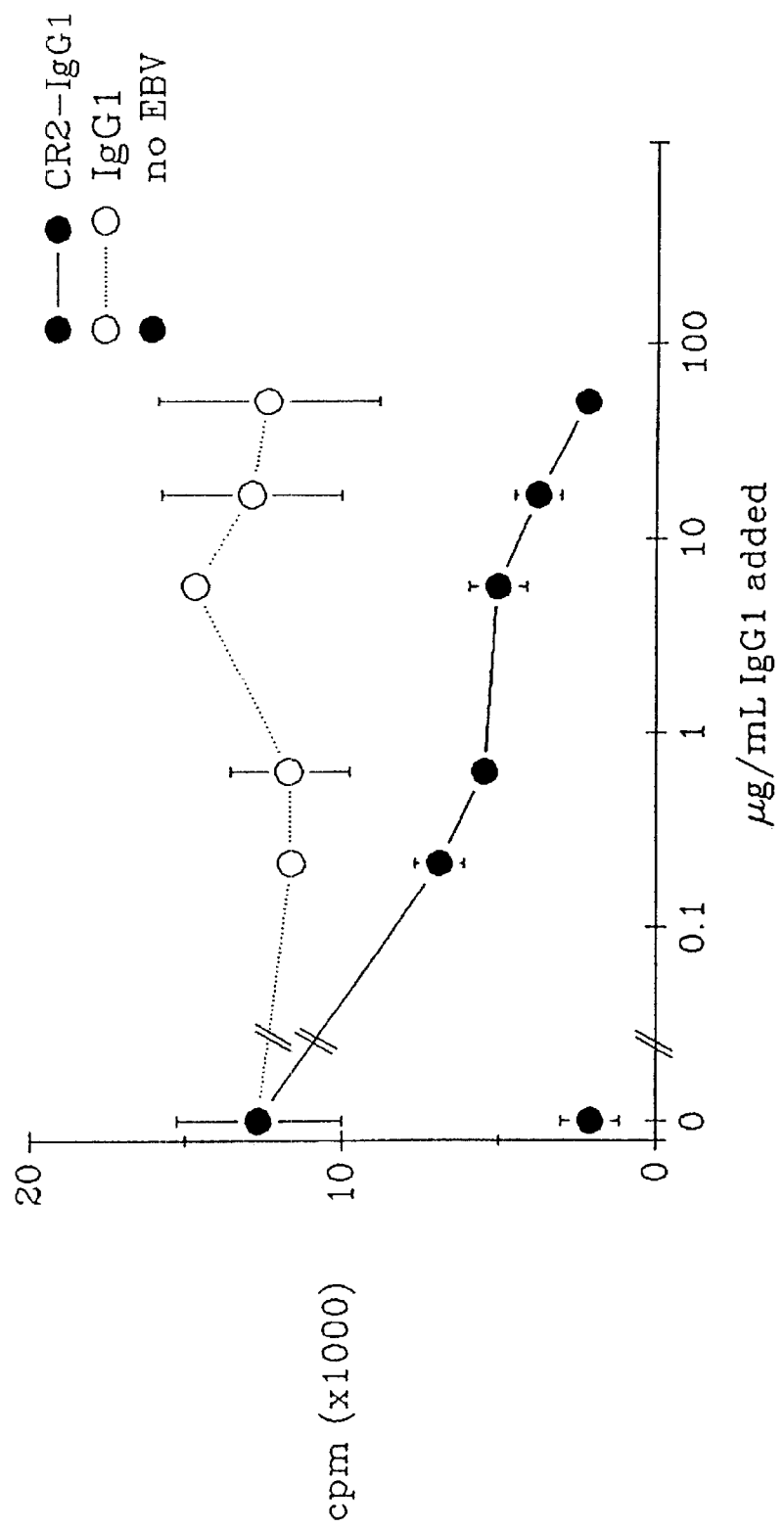
FIG. 6. CR2-IgG1 inhibits the infection of peripheral blood B-lymphocytes with EBV.

The outgrowth of EBV-infected B-lymphocytes, as expressed by incorporation of $^3$H-thymidine, was inhibited dose-dependently with complete inhibition at 50 ug/ml of CR2-IgG1 (FIG. 6).

EXAMPLE 5

Ability of CR2-IgG1 to Suppress Primary Response to Antigen

The murine models for complement-dependent antibody responses to T dependent and T independent antibody responses have been established (Matsuda, et al., (1978), *J. Immunol,* 121: 2048 and Martinelli, et al. (1978) *J. Immunol.* 121:2043).

BALB/c mice were obtained from the NCI breeding facility. They were rested for 1 week after arrival. For complement depletion, the mice were injected intraperitoneally with 20 ug of cobra venom factor (CVF) in 4 equal doses over 24 h before immunization. CR2-IgG1 and the control (irrelevant IgG1) were administered at the time of immunization together with the immunogen, fluorescein-Ficoll. This T independent antigen contained 91 molecules of fluorescein per carrier molecule. Mice were immunized with a low dose of fluorescein-Ficoll (8 ug) and a high dose (100 ug). On day 5 the mice were killed, blood samples were drawn and the spleen cells used for a PFC assay in which the resulting IgM and plaque forming cell (PFC) response was determined (Dintzis, et al., *J. Immunol* (1989), vol. 143, pp. 1239–1244). IgM levels are proportional to the mOD/min measured in the ELISA-system employed.

Figure 7:
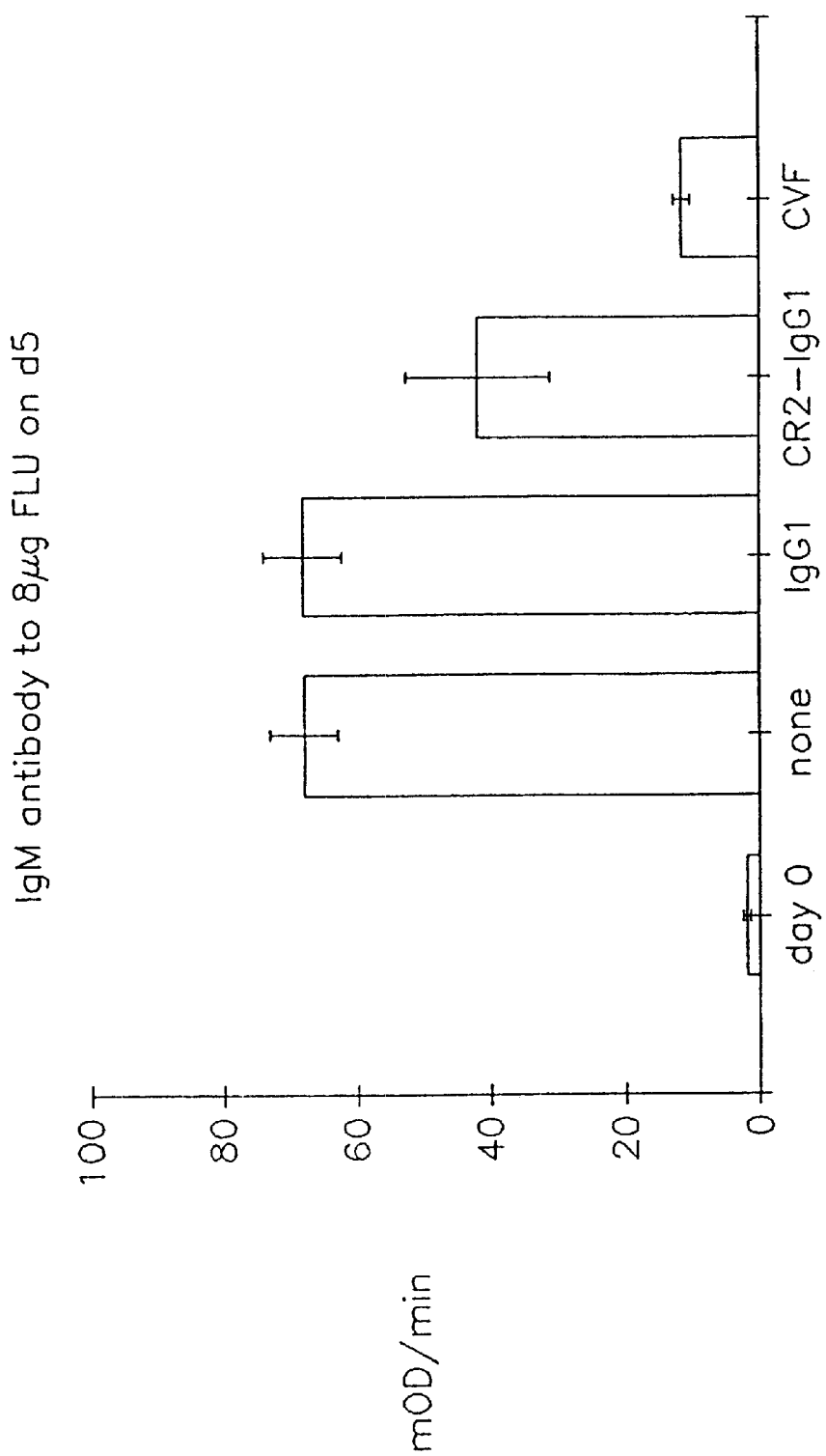
FIG. 7. The level of IgM specific to fluorescein is reduced upon treatment of mice with CR2-IgG1.
Figure 8:
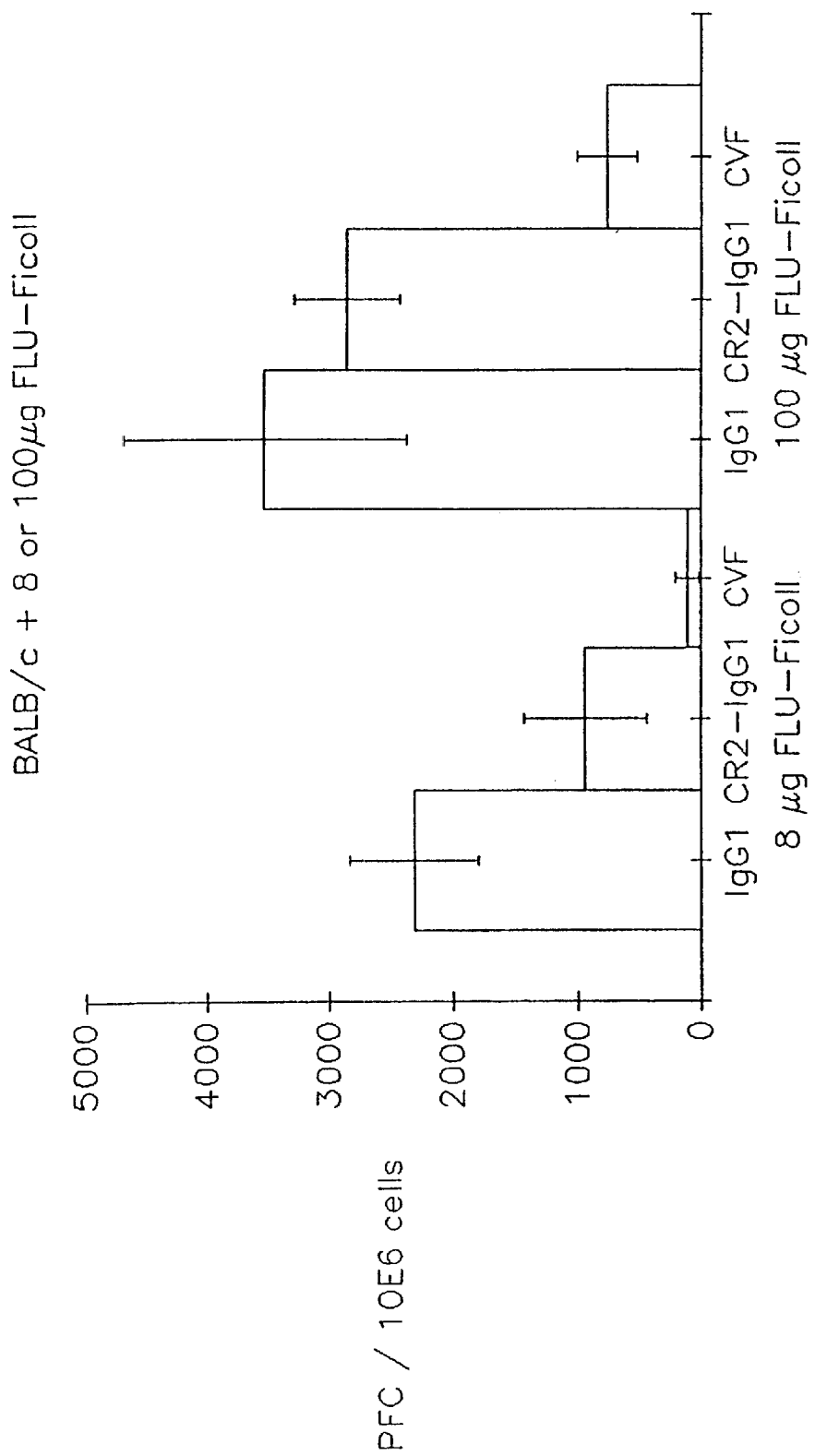
FIG. 8. The number of plaque forming cells generated in response to fluorescein-Ficoll and specific for fluorescein is reduced by CR2-IgG1.

CR2-IgG1, administered at the time of immunization, at a dose of 100 ug, reduced the IgM level from 67 mOD/min to 40. CVF resulted in a larger reduction to 15 mOD/min; background as determined on day 0 was 5 mOD/min (FIG. 7). The number of PFCs in spleens of CR2-IgG1 treated mice was also reduced by about 50%: control IgG1 treated mice yielded 3500/$10^6$ specific plaques, CVF treated mice 1000 and CR2-IgG1 treated mice 2200 (FIG. 8).

CVF is a protein from cobra venom, active as a convertase for C3. This enzyme depletes the injected mice of active C3 and thereby reduces the immune response to low doses of immunogens. CVF was included in these experiments as a positive control. The CR2-IgG1 fusion protein reduced the level of specific IgM produced and the number of PFC per spleen after immunization with 8 ug fluorescein-Ficoll by about 50% as compared to CVF. The response to 100 ug fluorescein-Ficoll was not significantly reduced, as has been observed for CVF (Martinelli, et al., (1978), *J. Immunol.,* 5:2052–2055).

The CR2-IgG1 effectively competed with cellular CR2 for the C3dg, presumably generated and bound to the antibody-antigen complexes during the immunization, thereby reducing the costimulatory role of CR2 on B cells. Because CR2-IgG1 was able to suppress the activation of B cells in vivo, it will be therapeutically useful in disease situations involving problematic antigen-specific B cell activation.

The effect of the CR2-IgG1 construct on the response of mice to an T-dependent antigen, sheep erythrocytes, was also measured. Three groups of BALB/c mice were assessed for their immune response to sheep erythrocytes (E): mice in the first group received a total of 800 ug of recombinant IgG1 in four divided doses given intravenously at 0 hr and intraperitoneally at 0.5 hr, 3 hr and 17 hr after immunization with $4\times10^5$ and $4\times10^6$ E, respectively; mice in the second group received CR2-IgG1 instead of the IgG1; and mice in the third group were depleted of C3 by treatment with cobra venom factor during the 24 hr prior to immunization. A fourth group of mice received only PBS and was not immunized with sheet E.

The protocol for injections of CR2-IgG1 and IgG1 was designed after preliminary metabolic studies had demonstrated an initial half-life of 2 hr for CR2-IgG1. On the fifth day after immunization, mice were assessed for the number of splenic direct plaque-forming cells (PFC) specific for sheep E, and for serum levels of IgM, IgG1, IgG2a, IgG2b and IgG3 anti-E. The control mice given the recombinant IgG1 responded in a dose-related manner to sheep E by increasing the number of splenic PFC and the serum concentrations of specific antibody among all isotypes measured, except IgG1 (FIG. 11). As has been reported previously, the specific antibody response was abolished by depleted mice of C3, indicating that, at the concentrations of antigen used in this experiment, the B cell response was dependent on the activation of this complement protein. The mice that had received CR2-IgG1 were as immunosuppressed as the C3-deficient mice, suggesting that cellular CR2 mediates the complement dependency of this T cell-dependent B cell response, and that the CR2-IgG1 is an effective suppressor of the antibody response to a T-dependent antigen.

Ability of CR2-IgG1 Construct to Inhibit Isotype Switching

To examine further the effect of the CR2-IgG1 chimera on the expression of the anti-E antibody among isotypes other than IgM, mice were assessed over a period of three to five weeks post-immunization with $4\times10^6$ E. Two groups of BALB/c mice received a total of 800 ug of IgG1 and CR2-IgG1, respectively, in five equally divided doses given intraperitoneally 1 hr prior to immunization, intravenously at the time of immunization, and intraperitoneally 0.5 hr. 3 hr and 17 hr after immunization; a third group received PBS and was not immunized with E. The cR2-IgG1 completely suppressed IgM anti-E at day five, after which no IgM of this specificity could be detected in any group (FIG. 12). The occurrence of anti-E among the various IgG isotypes, which peaked at later times and persisted for up to 40 days in the IgG1-treated mice, also was diminished by 50% to 70% in the mice treated with CR2-IgG1. Therefore, soluble CR2 inhibits the primary response and subsequent isotype switching to the T-dependent antigen, sheet E. The experiment was repeated in the C3H/HeJ strain, which is resistant to lipopolysaccharide (LPS), to exclude effects of possible LPS contamination of the recombinant provides, although none could be detected with the Limulus lysate assay at a sensitivity of greater than 0.16 ng/mg protein. The CR2-IgG1 was as immunosuppressive of the IgM and IgG responses to sheep E in the C3H/HEJ mice as it was in the BALB/c mice (FIG. 11). This demonstrates that the CR2-igG1 molecule is an effective immunosuppressive agent in vivo for inhibiting the primary B cell response to antigen.

EXAMPLE 6

Measurement of Half-Life of Labeled CR2 Constructs

Figure 13:
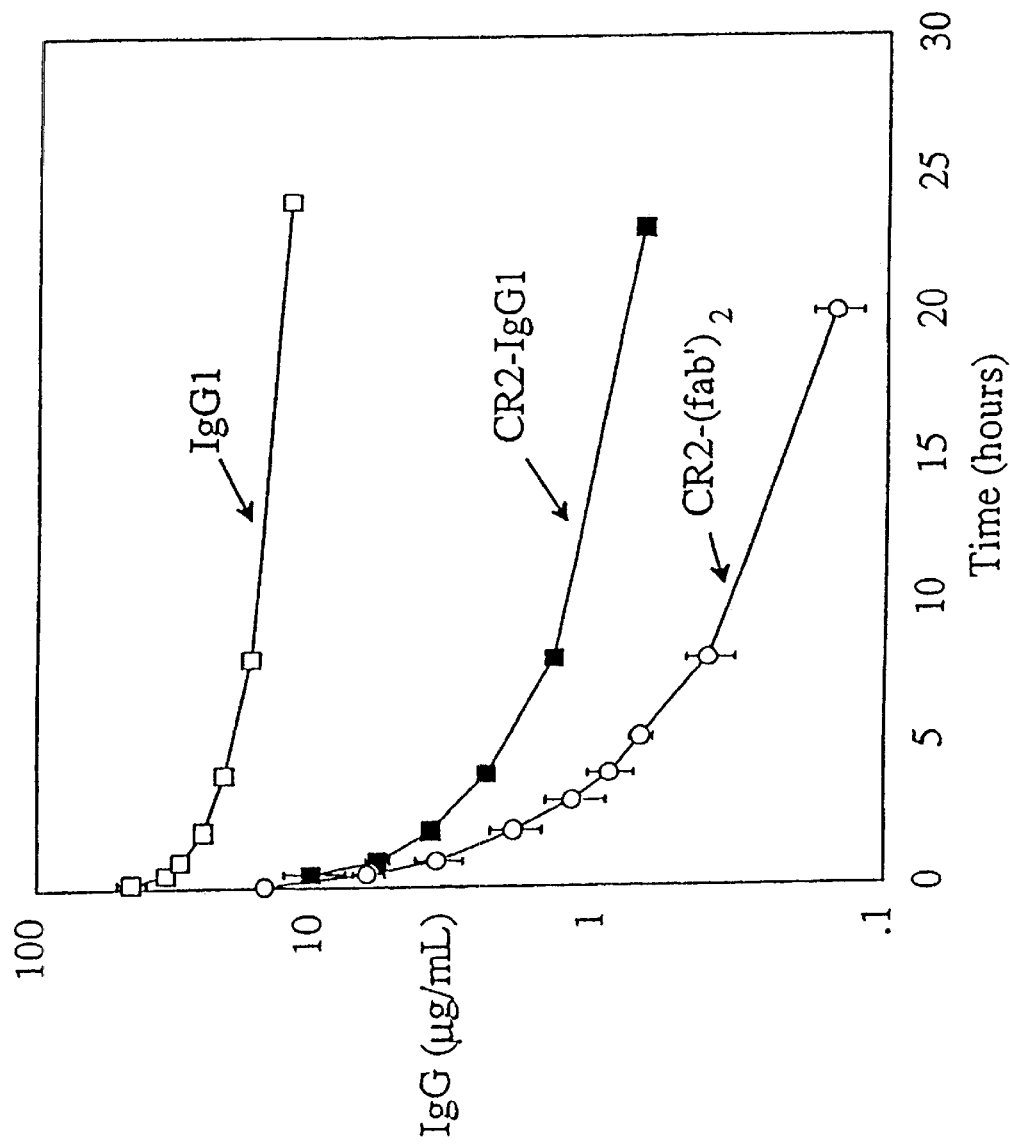
FIG. 13. Half-life in plasma of mice of $^{125}$I-labeled recombinant IgG1, CR2-IgG1, and CR2-F(ab')₂.

Recombinant IgG1, CR2-IgG1, and CR2-F(ab')$_2$ were radiolabeled with $^{125}$I and injected into mice. At various times blood was withdrawn and the radioactivity measured. The concentrations of the labeled species were calculated using the known specific radioactivity. The results are shown in FIG. 13. The decay is biphasic for each of the species. While the half-life of CR2-IgG1 was initially less than that of IgG1, between 10 and 20 hours their half-lives were similar. CR2-F(ab')$_2$ was cleared more rapidly than both IgG1 roCR2-IgG1. Therefore, fusion of SCRs of CR2 to the amino terminus of each heavy chain of IgG creates a molecule that retains much of the characteristic stability in vivo of immunoglobulin.

EXAMPLE 7

CR1-F(ab')$_2$ Construct Inhibits Complement Binding

CR1 contains 30 SCRs (short consensus repeats) in the F-allotype. The SCRs are arranged, among the first 28, as 4 groups of 7 SCRs. One of these groups (long homologous repeats) has a binding site for C4b and two have binding sites for C3b. SCRs numbered 8–11 (expected to contain C3b binding activity) were attached to the immunoglobulin heavy chain F(ab') according to the invention, by means of recombinant DNA techniques. A sequence corresponding to SCRs 8–11 of CR1 was produced by polymerase chain reaction amplification of a full length CR1 DNA clone using specific primers containing terminal Pst I recognition sequences. (The 27-mer 5' primer sequence= 5'CTGCAGCTGGGTCACTGTCAAGCC3'; the 42-mer 3' primer sequence= 5'GACCTGCAGTTGGACCTGGCTCACCCTGGAGCA GCTTGGTAG3'.) The amplified DNA was cut with Pst I and the resulting CR1 fragment was cloned into the Pst I site of a F(ab')$_2$ vector (Neuberger et al., 1984, Nature 312:604–608). The hybrid CR1-F(ab')$_2$ were expressed as protein by transfecting the recombinant plasmid into J558L cells and culturing the resulting cells in RPMI medium plus G418 plus 10% bovine calf serum. The expression of protein was determined by NIP coated ELISA assay. Expressed CR1-F(ab')$_2$ was purified by NIP-sepharose affinity chromatography, dialyzed in PBS and stored at –100° C. The resulting protein was assessed for their ability to inhibit the binding of C3b to human erythrocytes (E). As a point of comparison, the same inhibition study was done using soluble CR1 (sCR1).

Figure 14:
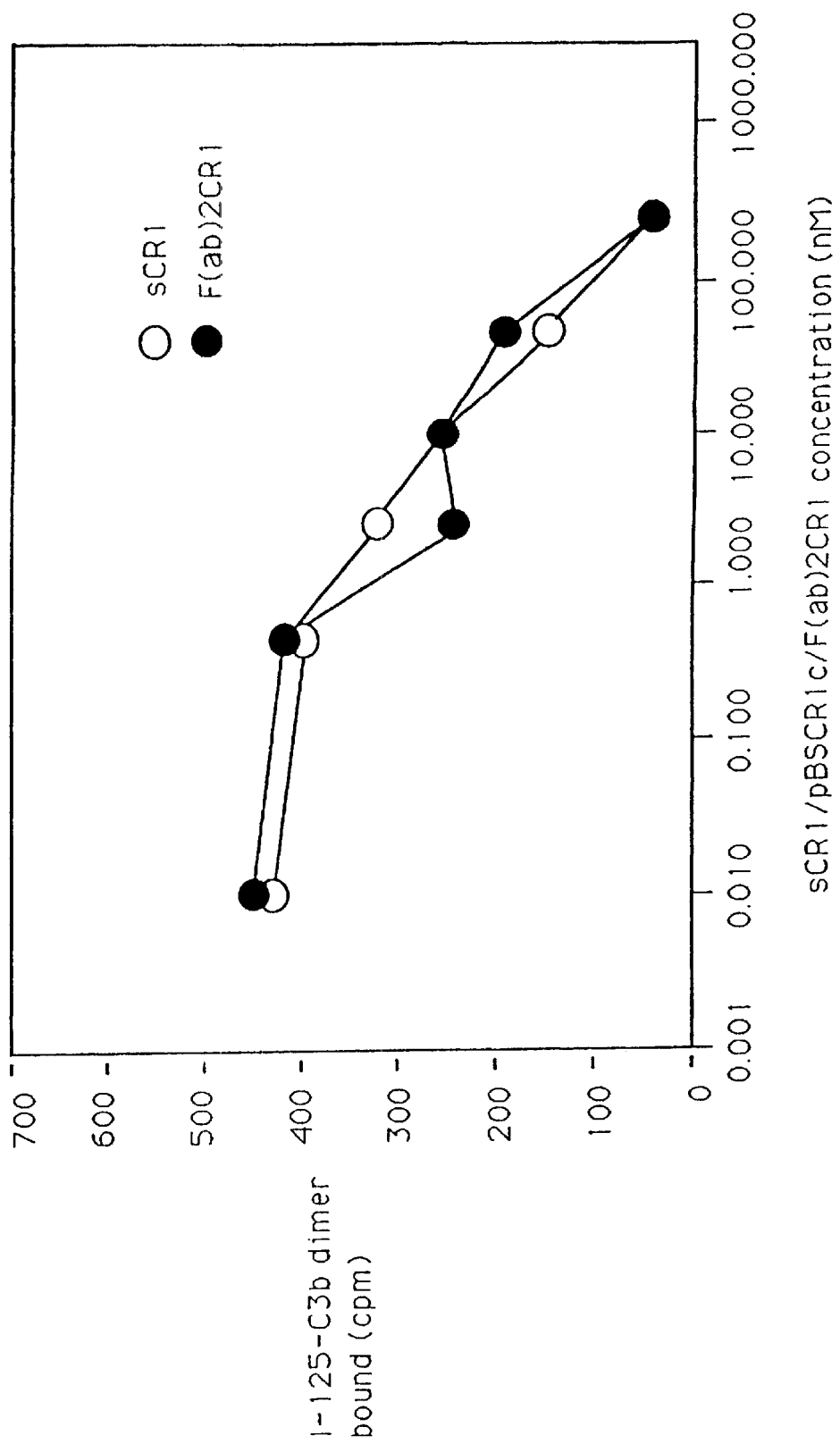
FIG. 14. Inhibition of binding of $^{125}$I-C3b-dimer to human E by sCR1/pBSCR1c and CR1-F(ab')₂ in which SCR-8 through -11 are attached to the immunoglobulin heavy chain.

C3b-dimers were radiolabed with $^{125}$I and incubated with human erythrocytes. Various amounts of sCRi/pBSCR1c or F(ab')$_2$-CR1 were added and the amount of $^{125}$I-C3b bound to the erythrocytes was determined. As shown in FIG. 14, both sCR1/pBSCR1 and F(ab')$_2$CR1 inhibit the binding of C3b-dimer to the same extent. This demonstrates that SCRs 8–11 contain a complete C3b binding domain of CR1. Thus, the full, bivalent C3b-binding function of sCR1/pBSCR1, which has 30 SCRs, can be achieved by attaching only four of these SCRs to each heavy chain of a F(ab')$_2$ construct.

EXAMPLE 8

CR1-F(ab')$_2$ Construct Does Not Inhibit The Classical Pathway of Complement

Figure 15:
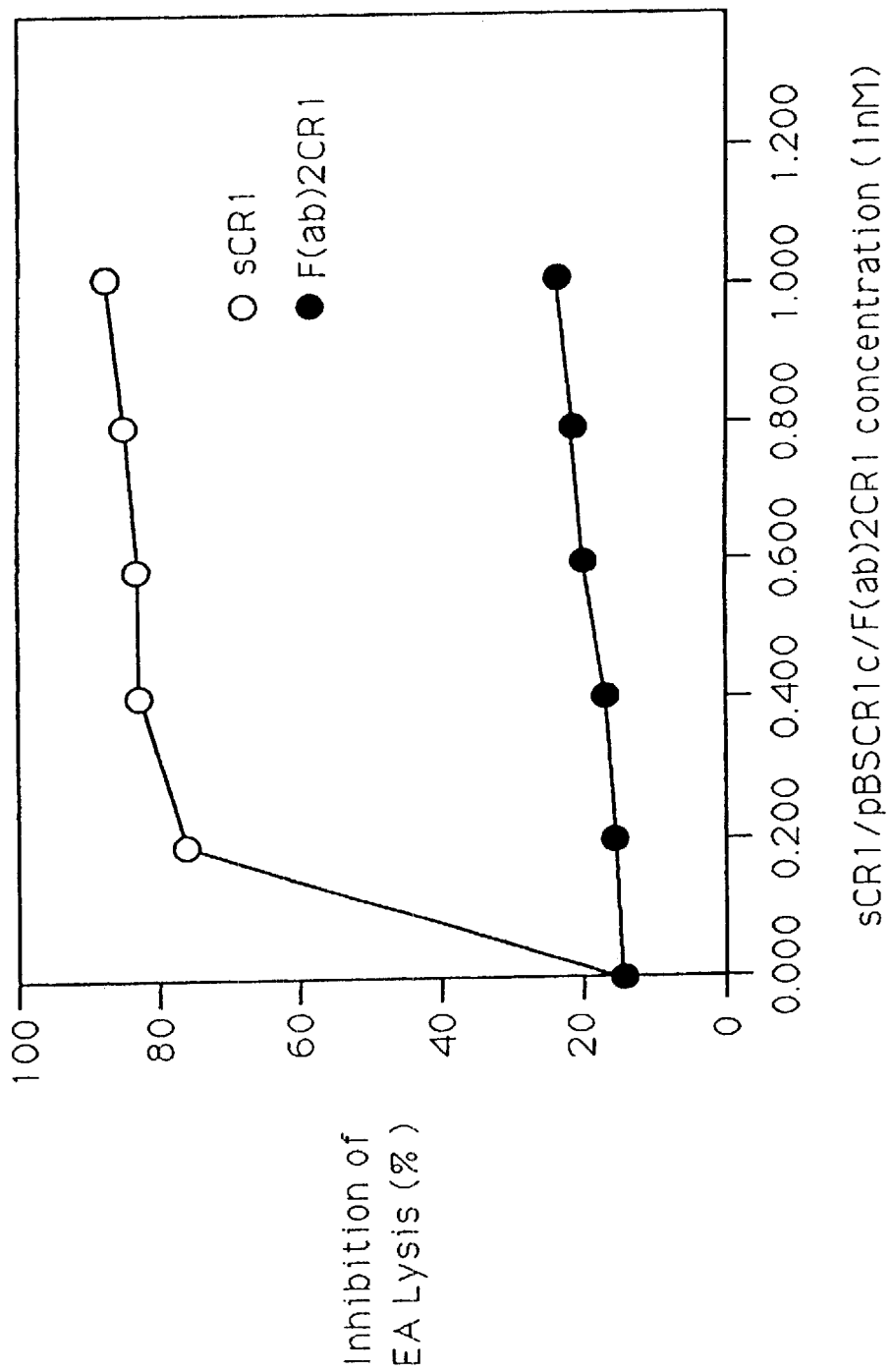
FIG. 15. Inhibition of lysis of antibody-sensitized sheep E in human serum by sCR1/pBSCR1c and CR1-F(ab')₂.

Antibody-sensitized sheep erythrocytes (EA) are lysed by activation of the classical pathway human complement. Soluble fragments of human CR1 inhibit this lysis by binding, and inactivating C4b and C3b of human complement. The ability of sCR1/pBSCR1c and F(ab')$_2$-CR1 to inhibit this lysis was also assayed. As shown in FIG. 15, sCR1/pBSCR1 almost completely inhibits the lysis. F(ab')$_2$-CR1 (containing only SCRs 8–11) inhibits to a much lesser extent. Presumably this is due to the absence of a C4b binding site on the construct. It is expected that the addition of SCRs that confer C4b-binding and C4b-inactivating function to CR1-F(ab')$_2$ will provide classical pathway inhibitory function as well.

EXAMPLE 9

CR1-F(ab')$_2$ Construct Inhibits the Alternative Pathway of Complement

Zymosan, a yeast cell wall preparation, activates the alternative pathway in human serum. The activation can be measured by radioimmune assay (RIA) for C3a or C5a. sCR1/pBSCR1c is known to inhibit this activation.

Figure 16:
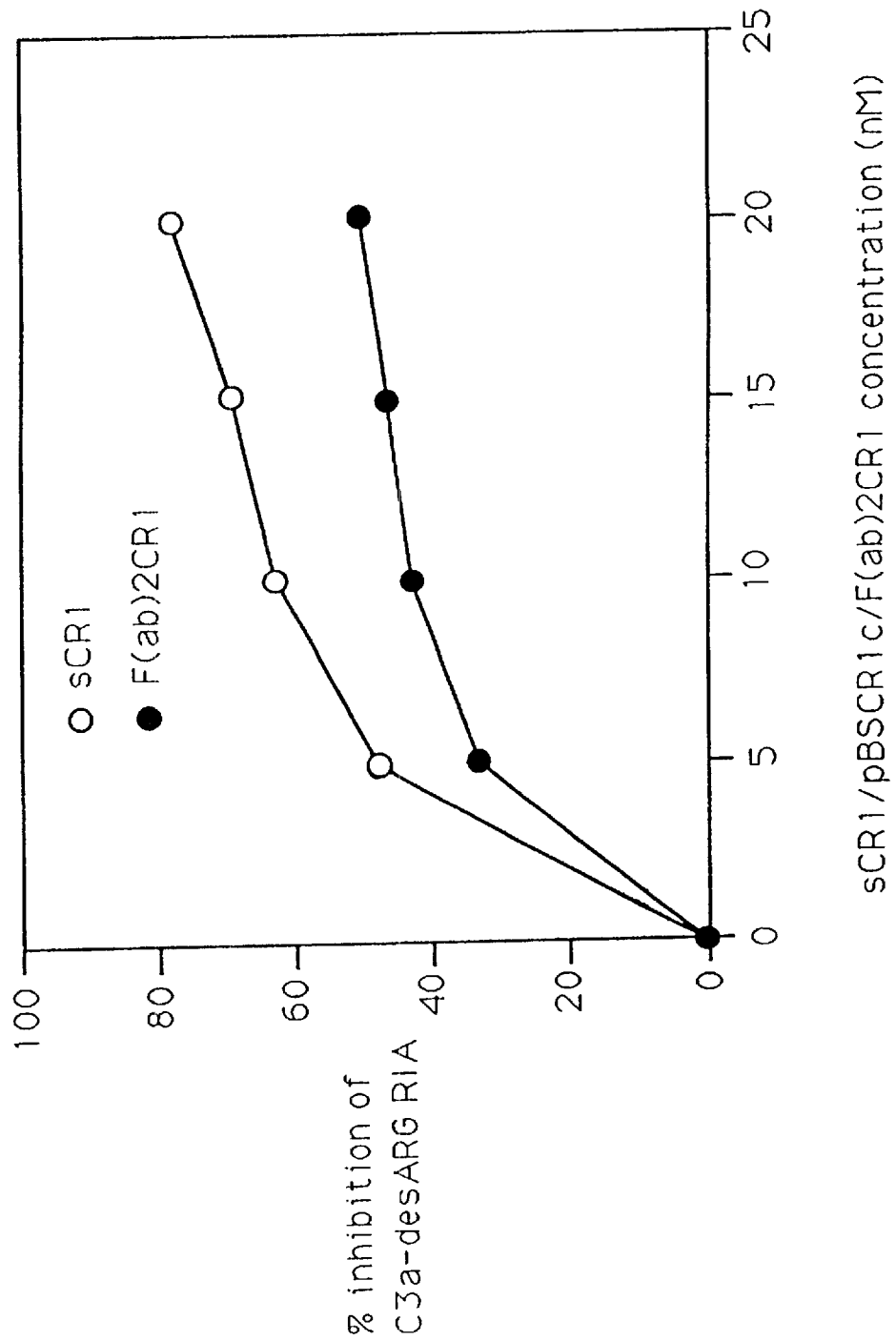
FIG. 16. Inhibition of C3a-desArg generation in zymosan-treatment human serum by sCR1/pBSCR1c and CR1-F(ab')₂.
Figure 17:
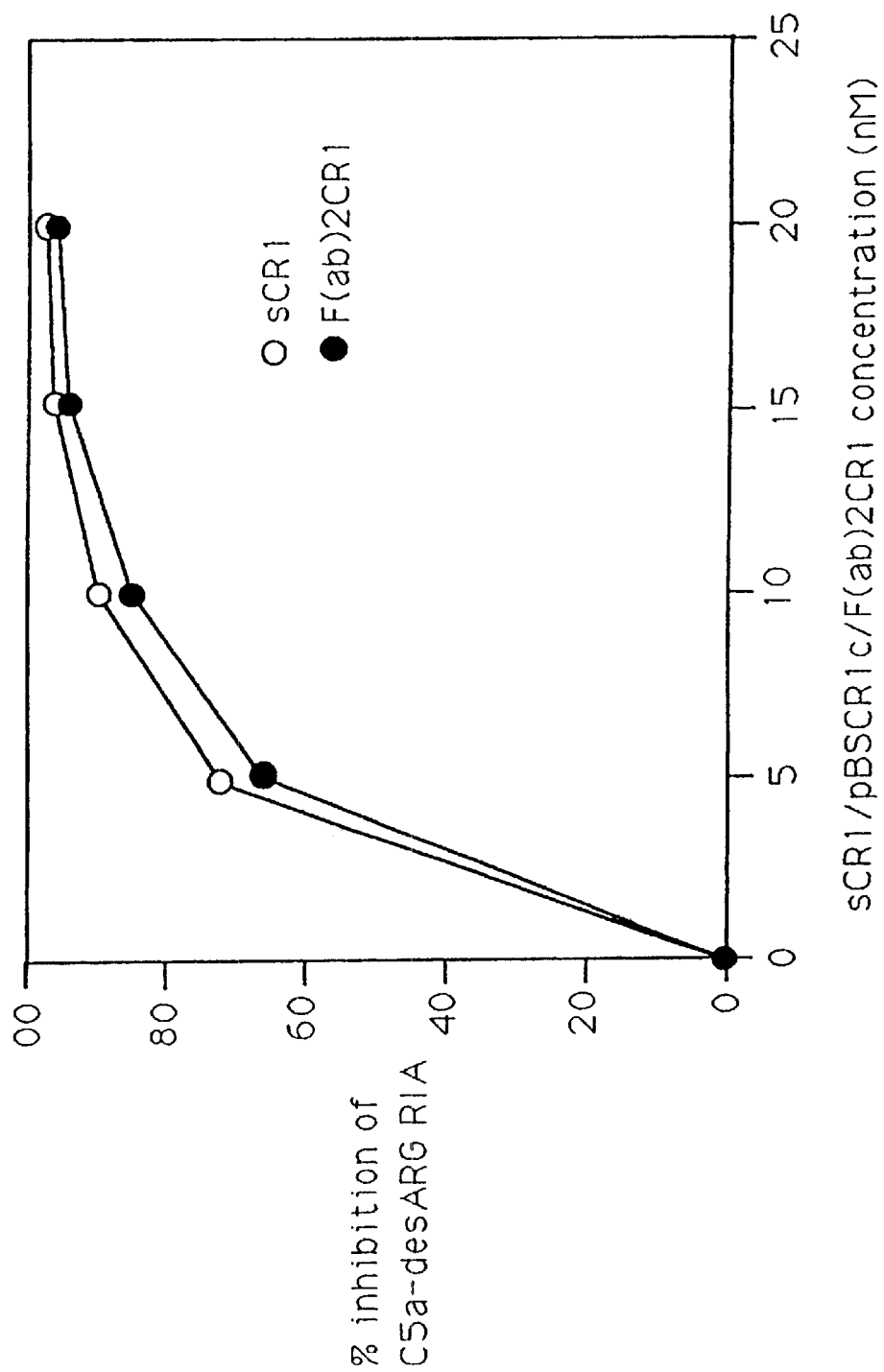
FIG. 17. Inhibition of C5a-desArg generation in zymosan-treated human serum by sCR1/pBSCR1c and CR1-F(ab')₂.

The ability of the F(ab')$_2$-CR1 construct to inhibit the activation of the alternative pathway by zymosan was measured and compared to that of sCR1/pBSCR1c. As shown in FIGS. 16 and 17, the F(ab')$_2$-CR1 inhibits C5a formation as well as sCR1/pBSCR1c and inhibits C3a almost as well as sCR1/pBSCR1.

These data indicate that the full alternative pathway inhibitory function of SCR1/pBSCR1 can be reproduced by transferring only SCRs 8–11 to the amino terminus of each heavy chain in the F(ab')$_2$ construct. These studies also indicate that, although these SCRs suffice for full alternative pathway inhibitory function, the addition of SCRs of the first long homologous repeat of CR1 that have C4b-binding and C4b-inactivating function will be necessary to achieve classical pathway inhibitory function.

What is claimed is:

1. A soluble construct comprising:
   (a) at least one polypeptide moiety comprising a fragment of a complement binding protein having a structure including short consensus repeats, said fragment including at least one short consensus repeat (SCR) of said complement binding protein, and
   (b) a soluble, physiologically-acceptable carrier molecule not including SCR structures, wherein said at least one polypeptide moiety (a) is bound to said carrier molecule (b), wherein said at least one polypeptide moiety includes a binding site of the complement binding protein, and wherein said soluble construct exhibits at least two binding sites.

2. The soluble construct according to claim 1, wherein the complement binding protein is selected from the group consisting of CR1, CR2, Factor H, C4-BP, DAF, and MCP.

3. The soluble construct of claim 2, wherein said soluble construct exhibits a C3b binding site and/or a C4b binding site.

4. The soluble construct according to claim 1, wherein the carrier molecule is selected from the group consisting of: serum albumin, heparin, immunoglobulin, polyethylene glycol, and polyoxyethylated polyols.

5. The soluble construct according to claim 1, wherein the carrier molecule is an immunoglobulin.

6. The soluble construct according to claim 5, wherein the carrier molecule is an immunoglobulin heavy chain.

7. The soluble construct according to claim 5, wherein the carrier molecule is an immunoglobulin heavy chain dimer.

8. The soluble construct according to claim 5, wherein the carrier molecule is an immunoglobulin of G1 isotype.

9. The soluble construct according to claim 5, wherein the carrier molecule is an immunoglobulin F(ab')$_2$ fragment.

10. The soluble construct according to claim 5, wherein said at least one polypeptide moiety is comprised of one or more SCRs of CR1 and/or one or more SCRs of CR2.

11. The soluble construct according to claim 10, comprising two polypeptide moieties selected from the group consisting of: SCRs 8–11 of CR1, LHR-A of CR1, LHR-B of CR1, LHR-C of CR1, and SCRs 1–2 of CR2.

12. A soluble complement inhibitor molecule comprising:
   (a) at least one polypeptide moiety comprising one or more short consensus repeat (SCR) structures of a complement protein selected from the group consisting of CR1, CR2, Factor H, C4-BP, DAF, and MCP, wherein said one or more SCR structures includes a binding site for a protein involved in complement activation, and
   (b) a soluble, physiologically acceptable carrier molecule, wherein said at least one polypeptide moiety (a) is bound to said carrier molecule (b), and wherein said soluble complement inhibitor molecule exhibits at least two such binding sites.

13. The soluble inhibitor molecule according to claim 12, wherein the carrier molecule is an immunoglobulin.

14. The soluble inhibitor molecule according to claim 13, wherein the carrier molecule is an immunoglobulin heavy chain.

15. The soluble inhibitor molecule according to claim 13, wherein the carrier molecule is an immunoglobulin heavy chain dimer.

16. The soluble inhibitor molecule according to claim 13, wherein the carrier molecule is an immunoglobulin of G1 isotype.

17. The soluble inhibitor molecule according to claim 13, wherein the carrier molecule is an immunoglobulin F(ab')$_2$ fragment.

18. The soluble inhibitor molecule according to claim 13, wherein said at least one polypeptide moiety is comprised of one or more SCRs of CR1 and/or one or more SCRs of CR2.

19. The soluble inhibitor molecule according to claim 18, comprising two polypeptide moieties selected from the group consisting of: SCRs 8–11 of CR1, LHR-A of CR1, LHR-B of CR1, LHR-C of CR1, and SCRs 1–2 of CR2.

20. A soluble complement inhibitor molecule comprising:
   (a) two or more contiguous short consensus repeat (SCR) structures of a complement receptor protein selected from the group consisting of CR1 and CR2, wherein said two or more SCR structures includes a binding site for a protein involved in complement activation, and
   (b) a soluble, physiologically acceptable carrier molecule, wherein said two or more SCR structures (a) are bound to said carrier molecule (b), and wherein said soluble complement inhibitor molecule exhibits at least two such binding sites.

21. The soluble complement inhibitor molecule of claim 20, wherein said complement receptor protein is CR1 and said two or more contiguous SCR structures are selected from the group consisting of SCRs 8–11, LHR-A, LHR-B and LHR-C.

22. The soluble complement inhibitor molecule of claim 20, wherein said complement receptor protein is CR2 and said two or more contiguous SCR structures are SCRs 1 and 2.

23. The soluble complement inhibitor molecule CR1-F(ab')$_2$, consisting essentially of an immunoglobulin G F(ab')$_2$ fragment with SCRs 8–11 of CR1 fused to the N-terminus of each heavy chain fragment.

24. The soluble complement inhibitor molecule CR2-IgG1, consisting essentially of an immunoglobulin gamma-1 with SCRs 1–2 of CR2 fused to the N-terminus of each heavy chain.

25. A method for inhibiting antigen-specific B cell activation in a mammal which comprises administering to said mammal the soluble inhibitor molecule according to any one of claims 22–24.

26. The soluble complement inhibitor molecule CR2-F(ab')$_2$, consisting essentially of an immunoglobulin G F(ab')$_2$ fragment with SCRs 1–2 of CR2 fused to the N-terminus of each heavy chain fragment.

27. A method for inhibiting Epstein-Barr virus (EBV) infection or EBV-induced conditions in a mammal which comprises administering to said mammal the soluble inhibitor molecule according to any one of claims 22, 24 or 26.

28. A therapeutic composition comprising the soluble construct according to any one of claims 1–24 in a pharmaceutically acceptable vehicle.

29. A method of treating a patient with a disease or immune disorder involving inappropriate or undesirable complement activation which comprises administering to the patient a soluble construct or inhibitor molecule according to any one of claims 1–24 in an amount sufficient to inhibit complement activation or complement-dependent cellular activation.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
       (A) LENGTH: 42 base pairs
       (B) TYPE: nucleic acid
       (C) STRANDEDNESS: unknown
       (D) TOPOLOGY: linear (ii) MOLECULE TYPE: cDNA (xi) SEQUENCE DESCRIPTION: SEQ ID NO:1:

```
GACCTGCAGT TGGACCTGGC TCACCCTGGA GCAGCTTGGT AG                    42
```

(2) INFORMATION FOR SEQ ID NO:2:

(i) SEQUENCE CHARACTERISTICS:
       (A) LENGTH: 272 base pairs
       (B) TYPE: nucleic acid
       (C) STRANDEDNESS: unknown
       (D) TOPOLOGY: linear (ii) MOLECULE TYPE: cDNA (ix) FEATURE:
       (A) NAME/KEY: CDS
       (B) LOCATION: 104..148

(ix) FEATURE:
       (A) NAME/KEY: CDS
       (B) LOCATION: 231..272

(xi) SEQUENCE DESCRIPTION: SEQ ID NO:2:

```
AAATCCTGTG TGTCTACAGT GGTAAATATA GGGTTGTCTA CACGATACAA AAAACATGAG      60

ATCACTGTTC TCTTTACAGT TACTGAGCAC ACAGGACCTC ACC ATG GGA TGG AGC       115
                                              Met Gly Trp Ser
                                                1

TGT ATC ATG CTC TTC TTG GCA GCA ACA GCT ACA GGTAAGGGGC TCACAGTAGC     168
Cys Ile Met Leu Phe Leu Ala Ala Thr Ala Thr
  5                  10                  15

AGGCTTGAGG TCTGGACATA TACATGGGTG ACAATGACAT CCACTTTGCC TTTCTCTCCA     228

CA GGT GTC CAC TCC CAG GTC CAA CTG CAG CTC GGG ATT TCT TGT           272
   Gly Val His Ser Gln Val Gln Leu Gln Leu Gly Ile Ser Cys
    1             5                   10
```

(2) INFORMATION FOR SEQ ID NO:3:

(i) SEQUENCE CHARACTERISTICS:
       (A) LENGTH: 15 amino acids
       (B) TYPE: amino acid
       (D) TOPOLOGY: linear (ii) MOLECULE TYPE: protein (xi) SEQUENCE DESCRIPTION: SEQ ID NO:3:

```
Met Gly Trp Ser Cys Ile Met Leu Phe Leu Ala Ala Thr Ala Thr
 1               5                  10                  15
```

(2) INFORMATION FOR SEQ ID NO:4:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:4:

```
Gly Val His Ser Gln Val Gln Leu Gln Leu Gly Ile Ser Cys
 1               5                  10
```

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..42

(xi) SEQUENCE DESCRIPTION: SEQ ID NO:5:

```
CCT CTC GAG GTG AGC CAG GTC CAA CTG CAG CAG CCT GGG GCT        42
Pro Leu Glu Val Ser Gln Val Gln Leu Gln Gln Pro Gly Ala
 1               5                  10
```

(2) INFORMATION FOR SEQ ID NO:6:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:6:

```
Pro Leu Glu Val Ser Gln Val Gln Leu Gln Gln Pro Gly Ala
 1               5                  10
```

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..48

(xi) SEQUENCE DESCRIPTION: SEQ ID NO:7:

```
GGT GTC CAC TCC CAG GTC CAA CTG CAG CTG GGT CAC TGT CAA GCC CCA       48
Gly Val His Ser Gln Val Gln Leu Gln Leu Gly His Cys Gln Ala Pro
 1               5                  10                  15
```

(2) INFORMATION FOR SEQ ID NO:8:

```
        (i) SEQUENCE CHARACTERISTICS:
            (A) LENGTH: 16 amino acids
            (B) TYPE: amino acid
            (D) TOPOLOGY: linear (ii) MOLECULE TYPE: protein (xi) SEQUENCE DESCRIPTION: SEQ ID NO:8:

Gly Val His Ser Gln Val Gln Leu Gln Leu Gly His Cys Gln Ala Pro
 1               5                  10                  15

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: unknown
            (D) TOPOLOGY: linear (ii) MOLECULE TYPE: cDNA (xi) SEQUENCE DESCRIPTION: SEQ ID NO:9:

CTGCAGCTGG GTCACTGTCA AGCC                                                24

(2) INFORMATION FOR SEQ ID NO:10:

(i) SEQUENCE CHARACTERISTICS:
            (A) LENGTH: 39 base pairs
            (B) TYPE: nucleic acid
            (C) STRANDEDNESS: both
            (D) TOPOLOGY: linear (ii) MOLECULE TYPE: cDNA (vi) ORIGINAL SOURCE:
            (A) ORGANISM: Homo sapiens (ix) FEATURE:
            (A) NAME/KEY: CDS
            (B) LOCATION: 1..39

(xi) SEQUENCE DESCRIPTION: SEQ ID NO:10:

CTA CCA AGC TGC TCC AGG GTG AGC CAG GTC CAA CTG CAG                       39
Leu Pro Ser Cys Ser Arg Val Ser Gln Val Gln Leu Gln
 1               5                  10

(2) INFORMATION FOR SEQ ID NO:11:

(i) SEQUENCE CHARACTERISTICS:
            (A) LENGTH: 13 amino acids
            (B) TYPE: amino acid
            (D) TOPOLOGY: linear (ii) MOLECULE TYPE: protein (xi) SEQUENCE DESCRIPTION: SEQ ID NO:11:

Leu Pro Ser Cys Ser Arg Val Ser Gln Val Gln Leu Gln
 1               5                  10
```